United States Patent
Davis et al.

(10) Patent No.: US 8,579,834 B2
(45) Date of Patent: Nov. 12, 2013

(54) DISPLAY OF DETECTED PATIENT POSTURE STATE

(75) Inventors: Jon P. Davis, St. Michael, MN (US); Duane L. Bourget, Albertville, MN (US); Mandla Shongwe, Brooklyn Park, MN (US); Rajeev M. Sahasrabudhe, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 166 days.

(21) Appl. No.: 12/985,965

(22) Filed: Jan. 6, 2011

(65) Prior Publication Data

US 2011/0172743 A1  Jul. 14, 2011

Related U.S. Application Data

(60) Provisional application No. 61/293,538, filed on Jan. 8, 2010.

(51) Int. Cl.
*A61B 5/103* (2006.01)
*A61N 1/365* (2006.01)
*A61B 5/11* (2006.01)
*A61B 5/00* (2006.01)

(52) U.S. Cl.
CPC .......... *A61N 1/36535* (2013.01); *A61B 5/1116* (2013.01); *A61B 5/0031* (2013.01)
USPC .............. 600/595; 600/509; 600/587; 607/19

(58) Field of Classification Search
CPC ............. A61B 5/00231; A61B 5/1116; A61N 1/36535
USPC ............................. 600/509, 587, 595; 607/19
See application file for complete search history.

(56) References Cited

U.S. PATENT DOCUMENTS

| 4,297,685 | A | 10/1981 | Brainard, II |
| 4,365,633 | A | 12/1982 | Loughman |
| 4,543,955 | A | 10/1985 | Schroeppel |
| 4,550,736 | A | 11/1985 | Broughton et al. |

(Continued)

FOREIGN PATENT DOCUMENTS

| DE | 19831109 | 1/2000 |
| DE | 10024103 | 11/2001 |

(Continued)

OTHER PUBLICATIONS

International Search Report and Written Opinion dated May 9, 2011 for corresponding PCT Application No. PCT/US2011/020564 (9 pgs.).

(Continued)

*Primary Examiner* — Christopher D Koharski
*Assistant Examiner* — Natasha Patel
(74) *Attorney, Agent, or Firm* — Shumaker & Sieffert, P.A.

(57) ABSTRACT

The disclosure provides a system that displays an indicator of patient posture state that changes according to posture state data. The posture state data may be transmitted from a medical device, for example, in or near real-time. In some examples, the disclosure relates to a method comprising receiving posture state data for a patient from a medical device; and presenting an indicator indicative of two or more of posture states based on the received posture state data, wherein each posture state of the two or more posture states is determined based on different detection criteria.

30 Claims, 22 Drawing Sheets

(56) References Cited

U.S. PATENT DOCUMENTS

| | | |
|---|---|---|
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,152,890 A * | 11/2000 | Kupfer et al. ............ 600/595 |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B2 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |

(56) References Cited

U.S. PATENT DOCUMENTS

| | | |
|---|---|---|
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0270163 A1 | 12/2005 | Littell |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |

(56) References Cited

U.S. PATENT DOCUMENTS

| | | |
|---|---|---|
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0137933 A1* | 5/2009 | Lieberman et al. ......... 600/595 |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0270747 A1* | 10/2009 | Van Dam et al. ......... 600/509 |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1* | 1/2010 | Panken ................. 600/587 |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1331022 A2 | 7/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

Muhannad Quwaider, Subir Biswas: "Body Posture Identification using Hidden Markov Model with a Wearable Sensor Network," Bodynets '08 Proceedings of the ICST 3rd International Conference on Body Area Networks, XP002632420, 2008 (8 pgs.).

"Analysis of heart rate dynamics by methods derived from non-linear mathematics: Clinical applicability and prognostic significance," http://herkules.oulu.fi.isbn9514250133/html, 4 pp., 2004.

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals,"http://www.minimitter.com.Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308,1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-51, 2004.

Buchser et al., "Improved Physical Activity in Patients Treated for Chronic Pain by Spinal Cord Stimulation," Neuromodulation, vol. 8, Issue 1, pp. 40-48, Mar. 2005.

(56) References Cited

OTHER PUBLICATIONS

Crago et al., "An Elbow Extension Neuroprosthesis for Individuals with Tetraplegia," IEEE Transactions on Rehabilitation Engineering, vol. 6, No. 1, pp. 1-6, Mar. 1998.
Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems, "ICECS 2002, $9^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
http://eis.comp.lances.ac.uk/fileadmin/relate/publications/2006-WearableSensors.pdf.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.

(56) References Cited

OTHER PUBLICATIONS

U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.
U.S. Appl. No. 12/895,919, filed Jan. 6, 2011, Davis et al.
U.S. Appl. No. 61/293,393, filed Jan. 8, 2010, Davis et al.
U.S. Appl. No. 61/330,063, filed Apr. 30, 2010, Davis et al.
U.S. Appl. No. 61/293,555, filed Jan. 8, 2010, Davis et al.
U.S. Appl. No. 12/986,039, filed Jan. 6, 2011, Davis et al.
Office Action for U.S. Appl. No. 12/433,103, dated Feb. 5, 2013, 8 pp.
Response to Non-Final Office Action dated Feb. 5, 2013, from U.S. Appl. No. 12/433,103, filed May 3, 2013, 14 pp.
Final Office Action from U.S. Appl. No. 12/433,103, dated Jun. 28, 2013, 11 pp.

* cited by examiner

DISPLAY OF DETECTED PATIENT POSTURE STATE

This application claims the benefit of U.S. Provisional Application No. 61/293,538 by Davis, entitled, "DISPLAY OF DETECTED PATIENT POSTURE STATE" and filed on Jan. 8, 2010, the entire content of which is incorporated herein by reference.

TECHNICAL FIELD

The disclosure relates to medical devices and, more particularly, to medical devices that detect patient posture state.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

Initially, a clinician uses an external device, e.g., a clinician programmer, to provide a set, or multiple sets, of stimulation parameters that instruct the medical device how to deliver the therapy to the patient. In the case of an implantable medical device, this "programming" task usually occurs once the medical device is implanted in the patient and ready for operation. In some cases, the initial stimulation parameters are the best estimate of the clinician as to what type of therapy will alleviate the patient of their physiological symptoms or conditions. The patient may thus need to visit the clinician periodically to subsequently adjust the stimulation parameters for more effective treatment.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure relates therapy systems including an external display device that presents graphical representations, such as, e.g., avatars and/or other indicators (e.g., graphical indicators) of patient posture state, to a user based on posture state data received from a medical device. The medical device could be an implantable medical device or an external medical device. In some examples, the medical device may be configured to deliver therapy to a patient according to the detected posture state of the patient. In such cases, the medical device may detect the posture state of a patient via a posture state module of the medical device. In other examples, the medical device may be configured to detect the posture state of a patient via a posture state module but not deliver therapy to the patient based on the detected posture state.

Based on posture state data, which in some examples may be received in or near real-time from the medical device, the external display device may present one or more indicators indicative of patient posture state to a user. In some examples, the external display may update an indicator of patient posture state substantially continuously (e.g., at a relatively high refresh rate) such that the posture state indicator reflects the posture state of the patient substantially simultaneously with actual patient movement.

In some examples, the external display device may present multiple indicators to represent two or more posture state, where each posture state is identified according to different posture state detection criteria. As one example, the external display device may present indicators for two or more of the real-time posture state, asserted posture state, and stable posture state of a patient. Each of the real-time posture state, asserted posture state, and stable posture state of the patient displayed by the external device may be determined based on posture state sensor data received from the posture state module of the medical device, although the detection criteria (e.g., detection algorithm) used to define each posture state from the sensor may be different for each type of posture state. In some examples, the external display may present indicators to represent both a stable posture state and unstable posture state of the patient.

In one example, the disclosure relates to a method comprising receiving posture state data for a patient from a medical device; and presenting an indicator indicative of two or more posture states based on the received posture state data, wherein each posture state of the two or more posture states is determined based on different detection criteria.

In another example, the disclosure relates to a display device comprising a processor that receives posture state data from a medical device; and a user interface that presents an indicator indicative of two or more posture states based on the received posture state data, wherein each posture state of the two or more posture states is determined based on different detection criteria.

In another example, the disclosure relates to a system comprising means for receiving posture state data for a patient from a medical device; and means presenting an indicator indicative of two or more posture states based on the received posture state data, wherein each posture state of the two or more posture states is determined based on different detection criteria.

In another example, the disclosure relates to a non-transitory computer-readable storage medium comprising instructions that cause one or more processors to receive posture state data for a patient from a medical device; and control a user interface to present an indicator indicative of two or more posture states based on the received posture state data, wherein each posture state of the two or more posture states is determined based on different detection criteria.

In another example, the disclosure is directed to a non-transitory computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein. The computer-readable storage medium may be an article of manufacture, and may be non-transitory.

The details of one or more aspects of the disclosure are set forth in the accompanying drawings and the description below. Other features, objects, and advantages will be apparent from the description and drawings, and from the claims.

DETAILED DESCRIPTION

Figure 1A:
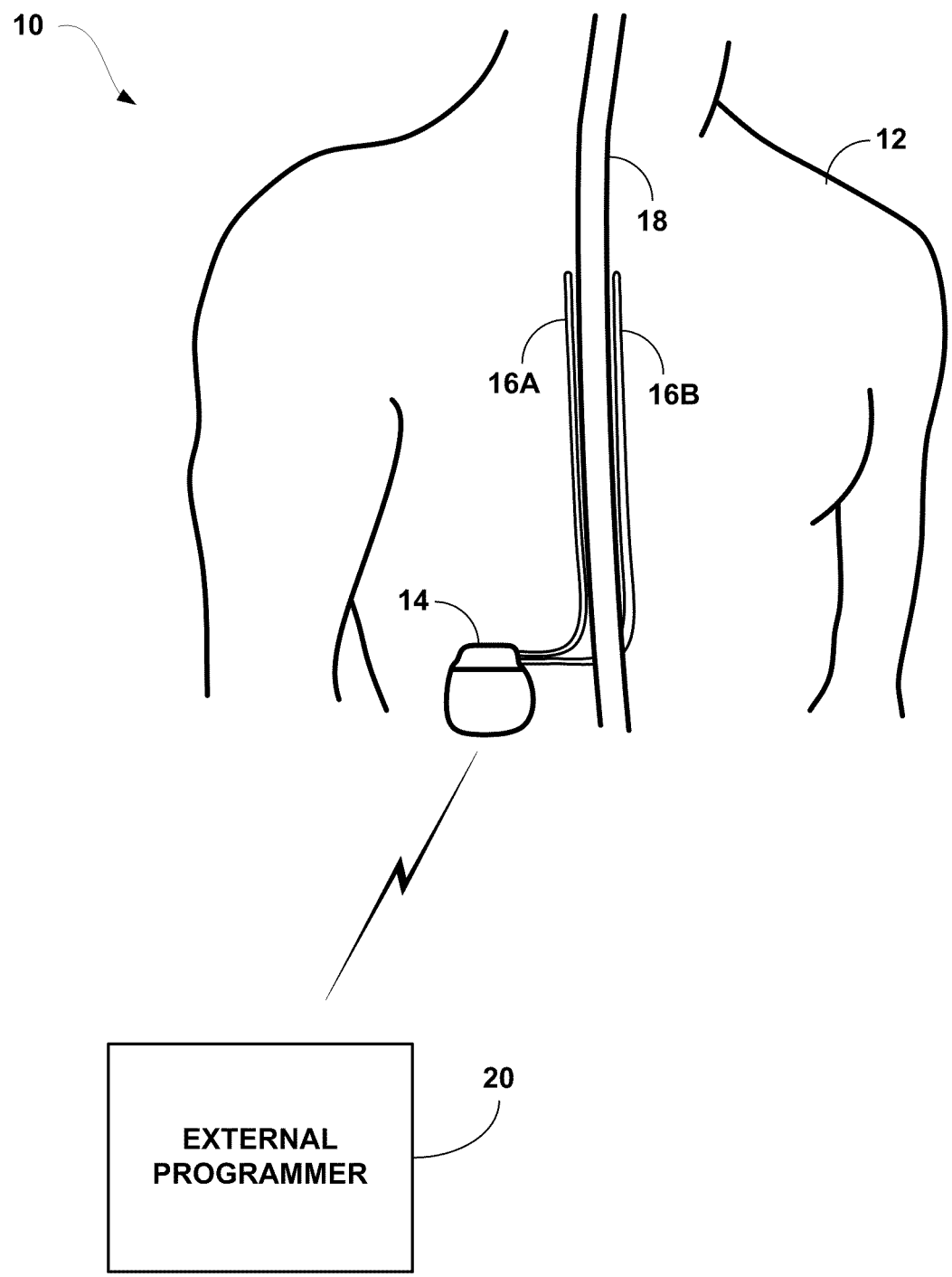
FIG. 1A is a conceptual diagram illustrating an example implantable stimulation system including two implantable stimulation leads.

As described above, in some examples, a medical device may be configured to deliver therapy based upon the posture state of the patient. For example, in the case of an IMD that delivers electrical stimulation therapy, the IMD may utilize information regarding the detected posture state of patient to determine what stimulation parameters are used for therapy to target certain symptoms that may change with different anatomical positions that may be occupied by a patient. These therapeutic changes due to posture states can be important to therapy programming, and it may be useful for the clinician and patient to visualize how patient physiological conditions (e.g., physiological symptoms) and the therapy delivered to the patient changes with the posture state of a patient.

Changes in the posture state of a patient receiving therapy from an IMD may cause changes in therapeutic efficacy. In some examples, such changes may be due to changes in distances between electrodes or other therapy delivery elements, e.g., due to temporary migration of leads or catheters with respect to patient physiology caused by forces or stresses associated with different postures of the patient, or from changes in compression of patient tissue in different posture states.

To maintain the delivery of effective therapy, it may be desirable to adjust therapy parameters based on different postures and/or activities engaged by the patient. In the case of electrical stimulation therapy delivered in pulses, therapy parameters may include amplitude (voltage or current), pulse rate, pulse width, electrode polarity, and electrode combination. Such therapy parameter values may be adjusted individually or by selecting different programs or groups of programs defining different sets of therapy parameters. Without posture-based therapy, the patient may need to continually manage therapy by manually adjusting the values of certain therapy parameters or selecting different therapy programs to achieve more efficacious therapy throughout many different posture states.

As described above, in some aspects, the disclosure relates to therapy systems including an external display device that presents graphical representations, such as, e.g, avatars and/or other indicators (e.g., graphical indicators) of patient posture state, to a user based on posture state data received from a medical device. In some examples, the medical device may be configured to deliver therapy to a patient according to the detected posture state of the patient. In such cases, the medical device may detect the posture state of a patient via a posture state module of the medical device.

The medical device may be an external or implantable medical device. Furthermore, while examples of the disclosure are described primarily with regard to an IMD or other medical device configured to deliver therapy to a patient based on the patient posture state, examples include medical devices configured to detect the posture state of a patient via a posture state module but not deliver therapy to the patient. For instance, a medical device configured to detect patient posture state may be used for diagnostic purposes, such as diagnosing a need for therapy, or determining how a patient is responding to existing therapy. In some examples, the medical may be configured to delivery therapy to a patient, but not on a posture state responsive basis.

Based on posture state data, which in some examples may be received in or near real-time from the medical device, the external display device may present one or more indicators indicative of patient posture state to a user. In some examples, the external display may update an indicator of patient posture state substantially continuously based on posture state data transmitted from a medical device in or near real-time such that the posture state indicator reflects the posture state of the patient substantially simultaneously with actual patient movement.

In some examples, the external display device may present multiple indicators to represent two or more patient posture states, where each posture state type is identified according to different posture state detection criteria. As one example, the external display device may present indicators for two or more of real-time posture state, asserted posture state, and stable posture state of a patient. Each of the real-time posture state, asserted posture state, and stable posture state of the patient displayed by the external device may be determined based on posture state sensor data received from the posture state module of the medical device, although the detection criteria (e.g., detection algorithm) used to define each posture state from the sensor may be different for each type of posture state.

In some examples, the external display may present indicators to represent both a stable posture state and unstable posture state of the patient based on received posture state data. The presentation of the indicators of the various types of patient posture state may allow a user to evaluate the performance of the medical device for detecting patient posture state, including evaluating the performance in terms of the temporal relationship between patient posture states derived from different posture state detection criteria.

An indicator for a posture state presented by the external display device may be a visible, audible or tactile indication delivered via a user interface associated with a programmer. A visible indication may be a graphical representation of the patient's posture state (which may include a patient posture or activity), a symbolic icon, a word, a number, or even arrows. An audible indication may be spoken words stating a posture state, different audible tones, different numbers of tones, or other audible information generated by the programmer to indicate the posture state. A tactile indication may be different numbers of vibratory pulses delivered in sequence or vibratory pulses of different lengths, amplitudes, or frequencies. Examples systems and techniques for presenting indicators indicative of a patient posture state to a user via an external display device may include one or more examples described in U.S. patent application Ser. No. 12/433,103, titled, "POSTURE STATE DISPLAY ON MEDICAL DEVICE USER INTERFACE" and filed on Apr. 30, 2009, the entire content of which is incorporated herein by reference.

As will be described further below, the posture state data that is transmitted to the external display device for posture state identification may include posture state parameter values generated by one or more posture state sensors used to sense the posture state of a patient. For example, in the case of a medical device including a three-axis accelerometer sensor to detect the posture state of a patient, the posture state parameters values may include sensor information from one or more of the x, y, and z signals generated by the three-axis accelerometer. The sensor information from the x, y, and z signals may include raw x, y, and z signal data, sampled values of the x, y, and z signals, and/or a sample sensed coordinate vector calculated from sampled signal values of the x, y, and z signals.

Such posture state data may be transmitted to the external display device or other computing device to determine the postures state of patient. For example, the external device may process the posture state data using one or more posture state detection algorithms reflecting desired detection criteria to determine patient posture state. In some examples, the external device may process the posture state data to determine one or more of the real-time posture state, asserted posture state, or stable posture state of a patient to determine the posture state indicators presented to a user on the display.

Additionally or alternatively, the posture state data received from the medical device may include an indication of one or more patient posture states, such as, the real-time patient posture state, asserted patient posture state, and/or stable patient posture state, as determined by the medical device prior to being transmitted to the external device. In such a case, the analysis and processing of the posture state sensor signal information may be performed by the medical device and then the identified posture state(s) of the patient may be transmitted to an external display for presentation of one or more indicators indicative of the identified posture state(s).

In some examples, the external display device may present an avatar or other graphical indicator directly representative of one or more sampled values of the x, y, and z signals of a posture sensor. For example, rather than analyzing sampled values of the x, y, and z signals of a posture sensor to characterize the values as a posture state that is defined to encompass a plurality of x, y, and z, values (which may be used to generate a sensed coordinate vector), the external display device may present an avatar or other graphical indicator to substantially match the sampled value(s) within a posture state space represented on the external display device. In some examples, the external display device or other device may convert sampled x, y, and z signal values into a sensed coordinate vector. The external device may then generated and present a graphical indicator to represent the particular sensed vector to a user on the external display. The external device may update the graphical indicator continuously or periodically to represent newly sampled sensor values and/or sensed coordinate vectors. In some examples, each sensed coordinate vector may be characterized as a unique posture state of the patient or a posture state of the patient may be defined to include a plurality of different sensed coordinate vectors.

In some examples, the posture state data may be streamed or otherwise transmitted from the medical device to the external display device in or near real-time, and the external display device may continuously or periodically update the presented indicators of patient state to reflect the posture state data received from the medical device. The timing of the posture state data transfer, as well as the rate at which indicator(s) of patient posture state are updated on the external display, may be such that any changes in the actual posture state of the patient are reflected substantially simultaneously by the real-time posture state indicator or other posture state indicator presented on the external display. In this manner, a user may be allowed to observe changes to patient posture state indicated by the real-time posture state indicator or other indicator to confirm that posture state data transmitted from the medical device is consistent with the actual posture state of a patient. In response to the one or more indicators presented by the external device, the clinician may monitor, adjust, or re-calibrate the posture state detection algorithm(s) to accurately represent the patient posture state.

In some examples, a medical device may characterize posture states of a patient as unstable or stable posture states using one or more suitable detection algorithms used to process sampled sensor signal data. In the case of a medical device configured to deliver therapy to a patient, it may be undesirable to modify or adjust therapy immediately upon the detection of sampled sensor signal data indicative of the patient transitioning from one posture state to another. For example, since a patient may move between two or more posture states in a relatively short period of time, the patient may not benefit from the relatively fast changes in therapy parameters that could accompany such movement if the therapy was changed for every posture state occupied by patient 12. As such, in some examples, only when patient 12 is within a posture state for a predetermined period of time does IMD 14 recognize the posture state as a stable posture state for changing therapy according to the detected patient posture state. In some cases, the predetermined amount of time may be referred to as a "dwell time." Until a posture state is determined to be a stable posture state, such a posture state may be referred to as an unstable posture state.

Although a medical device may adjust therapy based on changes to stable posture states, the medical device may monitor sampled signal data to detect unstable posture states of a patient. One example of an unstable posture state may be referred to herein as a "real-time posture state." A real-time posture state of a patient may refer to the posture state of a patient corresponding to one or more recently sampled sensor signal values. In some examples, a posture state detection algorithm may be configured to detect the real-time posture state of a patient based on the most recently sampled set of sensor signal values, or some rolling average of two or more recently sampled sets of sensor signals values. In this manner, the detection algorithm for use in detecting the real-time posture state of a patient may be such that the real-time posture state of a patient changes at a relatively high frequency and also tracks patient posture state movement with greater precision, e.g., as compared to a stable posture state.

Another example of an unstable posture state may be referred to herein as an "asserted posture state." An asserted posture state of a patient may refer to the posture state of a patient corresponding to a plurality of recently sampled sensor signals values that are processed using a sampling algorithm to determine the posture state of a patient. For example, for continuous sampling of sensor signals, a sampling algorithm may utilize a rolling sampling window that analyzes a preset number of recently sampled sets of sensor signal values (e.g., the five most recently sampled signal values). If the signal values within the sampling windows satisfy some preset criteria, (e.g., four of the five sets of values within the sampling window indicate the same posture state), then the medical device may make a positive detection of the posture state corresponding to the sets of values in the sampling window. One example of a sampling algorithm used to determine an asserted posture state of a patient may be referred to as an M of N filter. Other sampling algorithms are contemplated. In most cases, the detection criteria for the asserted posture state of a patient is such that it changes less frequently than the real-time posture state but more frequently than the stable posture state.

The detection criteria for unstable posture states versus stable posture states is such that changes to unstable postures states may be detected more frequently than changes to stable posture states. While such frequent changes can be undesirable for posture responsive therapy delivery, the unstable posture state(s) of a patient may be useful for more precisely tracking patient movement. In the example of an external display configured to continuously update a patient posture state based on posture state data, such as, sampled sensor signal values, the presentation of one or more indicators of unstable posture state(s) may be useful to better represent the movement of a patient in real-time, e.g., as compared to an indicator representative of the stable posture state due to the lag time that may accompany changes in a stable posture state compared to that of actual patient movement. Moreover, in some examples, the presentation of indicators of both stable and unstable posture states on the same temporal basis to a user may permit the user to gauge the performance of one or more detection algorithms in detecting patient posture state as well as gauge dwell times associated with one or more stable posture states.

One or more techniques for detecting and/or characterizing the posture state of a patient, in essence, as stable or unstable, or stable, real-time, and asserted, for example, may include one or examples described in U.S. patent application Ser. No. 12/433,004, titled "POSTURE STATE DETECTION SYSTEM AND METHOD," filed Apr. 30, 2009, the entire content of which is incorporated by reference herein.

In some examples, the external display device may also present the raw posture state data, and/or an activity level of the patient associated with the posture state. The external display device may also allow the clinician to adjust the values of one or more therapy parameters or adjust how the medical device detects the posture state of the patient receiving therapy. Further, the external display device may allow the user to review historical posture state data via a playback feature of a user interface of the display device. Although the display device may be any external computing device capable of presenting indicators of patient posture state on a display, the display device may also take the form of a patient or clinician programmer typically used to program and control delivered therapy.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. In some examples, the disclosure refers to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12. In the example of FIG. 1A, IMD 14 is an implantable electrical stimulator configured for spinal cord stimulation (SCS), e.g., for relief of chronic pain or other symptoms. Again, although FIG. 1A shows an implantable medical device, other embodiments may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another. In some examples, IMD 14 may be an internal or external device configured to monitor the posture state of a patient but not delivery therapy to patient 12. For example, IMD 14 may be an external device including one or more accelerometers worn by patient 12 to monitor patient posture state over a period of time based on the signal(s) generated by the one or more accelerometers.

Although FIG. 1A is directed to SCS therapy, system 10 may alternatively be directed to any other condition that may benefit from stimulation therapy. For example, system 10 may be used to treat tremor, Parkinson's disease, anxiety, depression, epilepsy, urinary or fecal incontinence, sexual dysfunction, obesity, or gastroparesis. In this manner, system 10 may be configured to provide therapy taking the form of deep brain stimulation (DBS), peripheral nerve stimulation, pelvic floor stimulation, gastric stimulation, or any other stimulation therapy. Patient 12 is ordinarily a human patient.

Each of leads 16 may include one or more electrodes (not shown in FIG. 1A), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described in this disclosure for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing.

The stimulation may be delivered via selected combinations of electrodes carried by one or both of leads 16. The target tissue may be any tissue affected by electrical stimulation energy, such as electrical stimulation pulses or waveforms. Such tissue includes nerves, smooth muscle, and skeletal muscle. In the example illustrated by FIG. 1A, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 may deliver stimulation therapy according to one or more programs. A program defines one or more stimulation parameters that define an aspect of the therapy delivered by IMD 14 according to that program. For example, a program that controls delivery of stimulation by IMD 14 in the form of pulses may define one or more therapy parameters such as a voltage or current pulse amplitude, a pulse width, a pulse rate, for stimulation pulses delivered by IMD 14 according to that program. Moreover, therapy may be delivered according to multiple programs, wherein multiple programs are contained within each of a multiple of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdominal pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. For example, stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy.

Also, posture state changes may present changes in pain level. In some examples, to avoid interruptions in effective therapy, IMD 14 may include a posture state module that detects the patient posture state. The IMD automatically adjusts stimulation according to the detected posture state of patient 12, thereby providing posture state responsive therapy. For example, the posture state module may include one or more accelerometers that detect when patient 12 occupies a posture state in which it is appropriate to decrease the stimulation amplitude, e.g., when patient 12 lies down. The IMD may automatically reduce stimulation amplitude so that patient 12 does not manually have to do so. Example posture states may include "Upright," "Upright and Active," "Lying Front," "Lying Left," "Lying Right," "Lying Back," and the like.

In some examples, IMD 14 provides posture responsive therapy, e.g., IMD 14 or an external programmer 20 detects changes in patient posture and automatically adjusts therapy based on the patient posture. These therapy adjustments may be manually programmed in IMD 14 or an external programmer 20, e.g., a clinician may specify one or more therapy programs for each patient posture. In addition, automatic therapy adjustments due to changes in patient posture may also be based on recorded associations between manual patient therapy adjustments and patient posture, e.g., IMD 14 or an external programmer 20 associate manual patient therapy adjustments with patient postures and then automatically repeat those therapy adjustments for the corresponding patient postures.

In response to a posture state detected by the posture state module, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In other cases, IMD 14 may automatically increase stimulation amplitude based on posture state. In some cases, IMD 14 may communicate with external programmer 20, e.g., a display device, to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1A, a user, such as a clinician or patient 12, may interact with a user interface of the display device, e.g., external programmer 20, to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, in the case of electrical stimulation therapy including stimulation pulses, a program may be characterized by an electrode combination, electrode polarities, voltage or current amplitude, pulse width, pulse rate, and/or duration. A group may be characterized by multiple programs that are delivered simultaneously or on an interleaved or rotating basis.

The user interface of external programmer 20 may present an indicator to indicate to the user the posture state in which the patient 12 currently occupies. This patient posture state may be a static posture that does not take into account activity level, an activity level that does not take into account posture, or some combination of the posture and activity level that describes the physical position and movement of patient 12. As an example, posture may be characterized as one of the following postures: standing, sitting, lying down on back, lying down on front, lying down on left side, lying down on right side. Activity level may be characterized as one of: high, medium and low, or, e.g., walking, biking, running, or the like.

Posture state may indicate a combination of one of the above postures with one of the above activity levels. For some postures, such as lying down postures, the posture state may not need to consider activity level, as the patient may be less likely to undertake any significant activity in such postures. In other cases, all posture states may take into account posture and activity level, even if there is minimal activity in a particular posture. Posture state may be determined based on detected posture information and/or activity level information generated by a posture state module, which may include one or more accelerometers or other posture or activity level sensors. System 10 may utilize fewer or more different types of posture states depending upon the needs of patient 12.

The patient posture state may be represented by an avatar of patient 12 or some other posture state indicator presented to patient 12 and generated by the user interface of programmer 20 as a visible, audible, or tactile indication. As described above, in some cases, a patient posture state may include a real-time patient posture state, an asserted patient posture state, and a stable patient posture state. In some examples, programmer 20 presents and updates one or more posture state indicators substantially continuously according to data transmitted in or near real-time from IMD 14. When presented as a different visible indication, a posture state indication may be, for example, a graphical representation, a symbolic icon, a textual representation such as word or number, an arrow, or any other type of indication. An avatar (e.g., a three-dimensional avatar) and other visible indications of patient posture state may be presented via a display, such as an a liquid crystal display (LCD), dot matrix display, organic light-emitting diode (OLED) display, touch screen, or the like. In other cases, a visible indication may be provided in a translucent area that is selectively backlit to indicate a posture. An audible indication may also be produced by programmer 20 to supplement a graphical indicator as spoken words stating a posture state, or different audible tones, different numbers of tones, or other audible information generated by the programmer to indicate posture state. Additionally, a tactile indication may be produced by programmer 20 different numbers of vibratory pulses delivered in sequence or vibratory pulses of different lengths, amplitudes, or frequencies for the benefit of patient 12 during therapy.

IMD 14 may transmit posture state data to programmer 20 in a continuous real-time manner. However, IMD 14 may also transmit posture state data on a periodic or intermittent basis or in response to a posture state change. Alternatively, programmer 20 may request a posture state detection from IMD 14 on a periodic, intermittent or continuous basis. The posture state data provided from IMD 14 to programmer 20 may be a posture state value that is raw data later interpreted to identify the posture state of patient 12, or simply a post-processed indication of the detected posture state, e.g., upright, lying front, lying back, lying left, lying right, or the like. In some examples, the raw data may be processed via according to different detection criteria, e.g., to determine one or more of real-time posture state, asserted posture state, and/or stable posture state of a patient based on the raw sensor data. External programmer 20 then may generate and present a posture state indicator in the appropriate configuration to represent the corresponding posture state based upon the posture state data transmitted from IMD 14 in real-time. In some examples, the indicator presented by external programmer to a user may be representative a particular sensed coordinate vector (e.g., in the case of sampled x, y, and z axis sensor values).

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use. In examples in which IMD 14 is configured to monitor patient posture state but not delivery therapy, programmer 20 may be used to display posture state information to a user but not program therapy delivery. In any case, external programmer 20 may be a display device that presents an indicator of one or more posture state of patient 12. In some examples, the indicator of patient posture state be reflective of postures state data received in or near real-time from IMD 14.

In general, as will be described below, external programmer 20 may be one example of a display device including a processor that receives posture state data from a medical device; and a user interface that presents an indicator indicative of two or more posture states based on the received posture state data, where each posture state of the two or more posture states is determined based on different detection criteria.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal tips of leads 16 are one or more electrodes (not shown) that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Figure 1B:
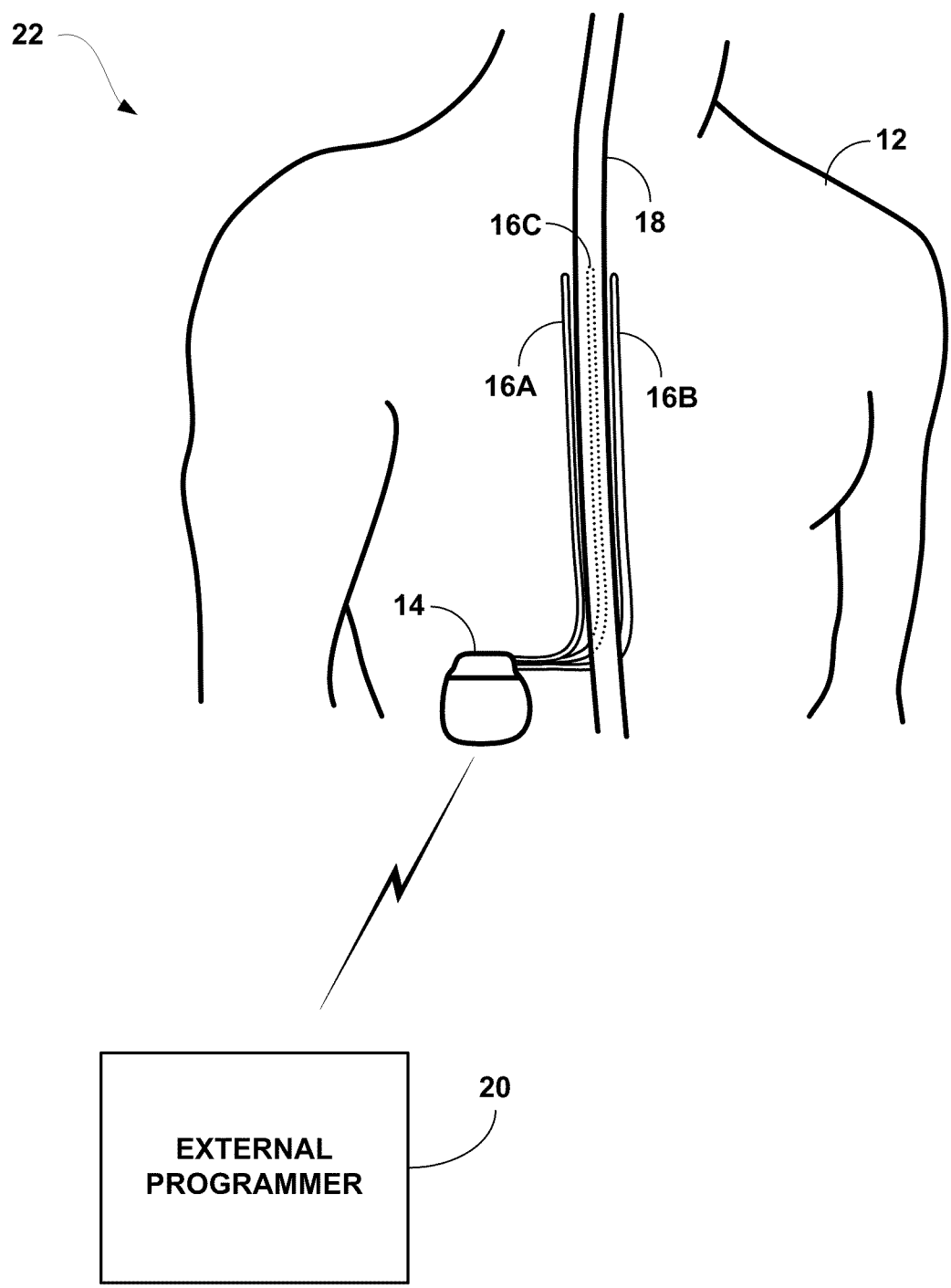
FIG. 1B is a conceptual diagram illustrating an example implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. A user may initially communicate the number and configuration of leads 16 to external programmer 20 in order to appropriately program stimulation therapy.

For example, leads 16A and 16B could include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
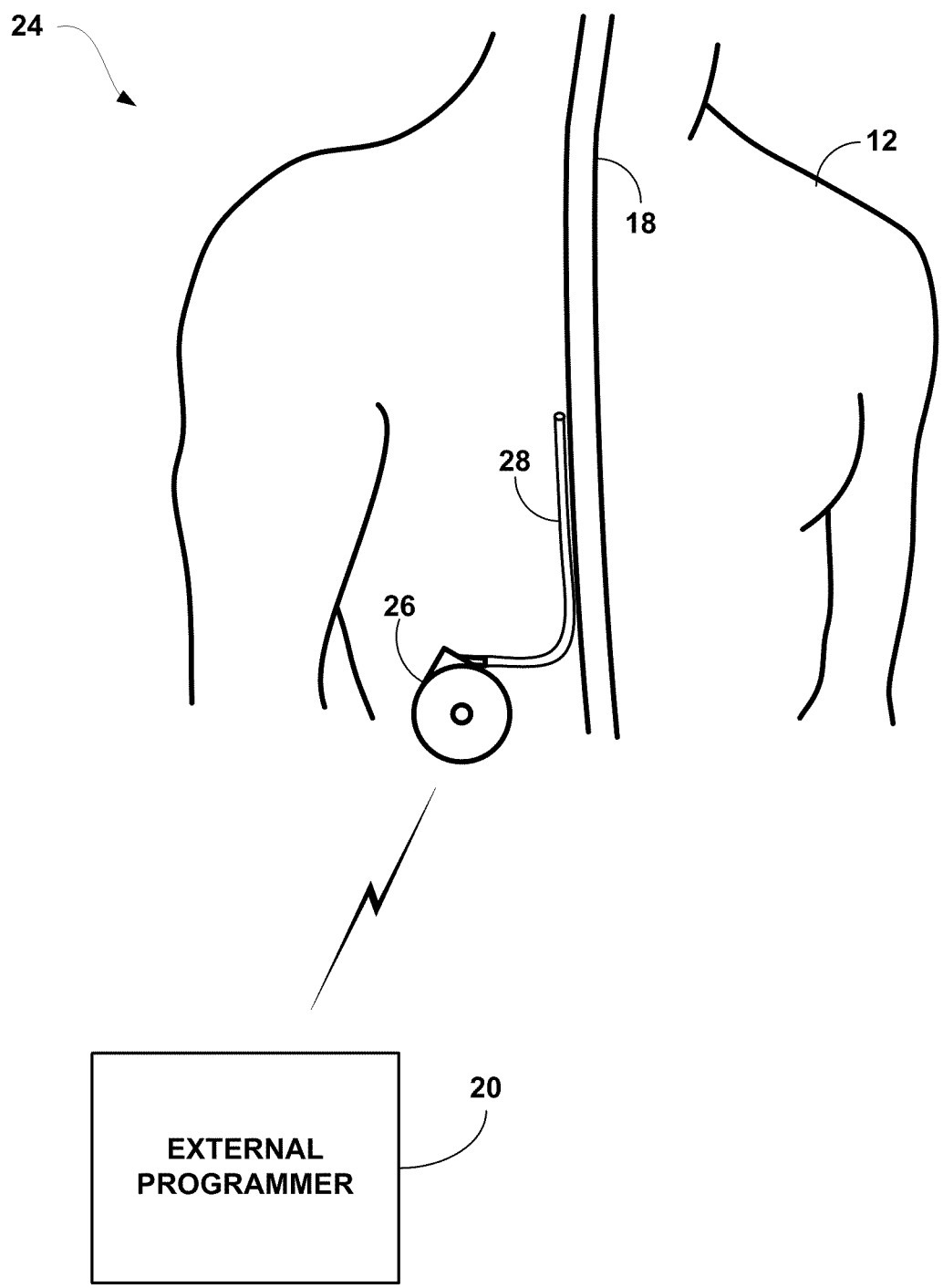
FIG. 1C is a conceptual diagram illustrating an example implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of drug stimulation therapy instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some embodiments, IMD 26 may be an external device which includes a percutaneous catheter that forms catheter 28 or that is coupled to catheter 28, e.g., via a fluid coupler. In other embodiments, IMD 26 may include both electrical stimulation as described in IMD 14 and drug delivery therapy.

IMD 26 may also operate using therapy parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Similar to IMD 14, IMD 26 may include a posture state module that monitors the patient posture state. IMD 26 may adjust therapy based on posture state. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
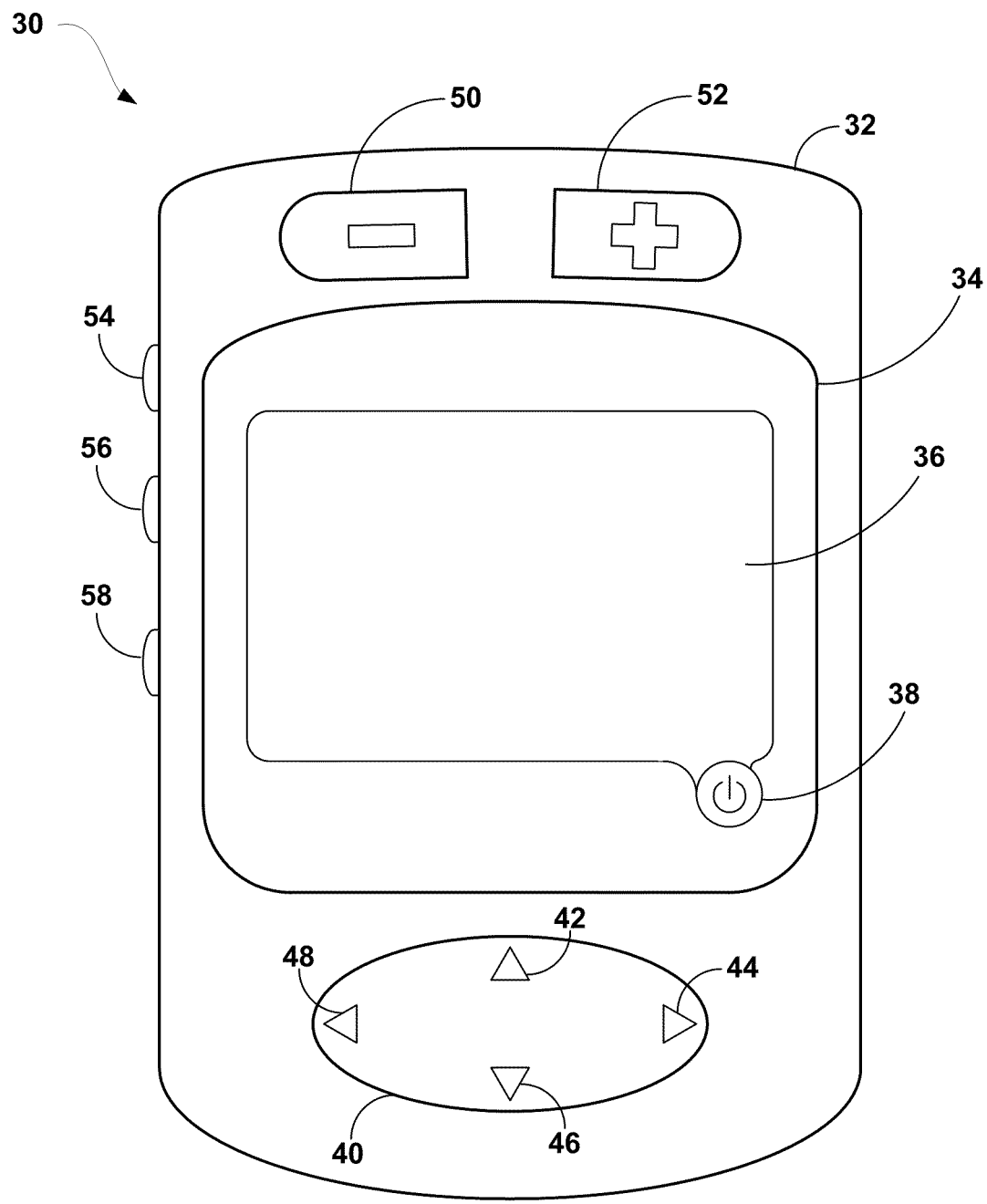
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an implantable medical device. Patient programmer 30 is an external device and an example embodiment of external programmer 20 illustrated in FIGS. 1A, 1B and 1C and may be used with either IMD 14 or IMD 26. In alternative embodiments, patient programmer 30 may be used with an external medical device. As shown in FIG. 2, patient programmer 30 provides a user interface (not shown) for a user, such as patient 12, to manage and program stimulation therapy. In addition, patient programmer 30 may present one or more indicators of the posture state of patient 12, e.g., in or near real-time, in order to represent the patient posture state to a user. Although patient programmer 30 may limit some programming features for patient 12, programmer 30 may display example user interfaces 200, 232, or 250 described herein. Patient programmer 30 is protected by housing 32, which encloses circuitry necessary for patient programmer 30 to operate.

Patient programmer 30 also includes display 36, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which allows a user to navigate through items displayed on display 36 in the direction of arrows 42, 44, 46, and 48. In some embodiments, the buttons and pad 40 may take the form of soft keys (e.g., with functions and contexts indicated on display 36), with functionality that may change, for example, based on current programming operation or user preference. In alternative embodiments, display 36 may be a touch screen in which patient 12 may interact directly with display 36 without the use of control pad 40 or even increase button 52 and decrease button 50.

In the illustrated embodiment, patient programmer 30 is a hand held device. Patient programmer 30 may accompany patient 12 throughout a daily routine. In some cases, patient programmer 30 may be used by a clinician when patient 12 visits the clinician in a hospital or clinic. In other embodiments, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52, respectively. In some embodiments, illumination of display 36 may be controlled by a knob that rotates clockwise and counter-clockwise. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may be a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display 36 may present a visible posture state indication based on the posture state(s) detected by IMD 14. In some examples, this posture state indication may be the avatar of patient 12 or other graphical indicator updated continuously in or near real-time according to posture state data transmitted from IMD 14. However, patient programmer 30 may typically present other posture state indications such as a small icon or text representation along with regular therapy.

Further, display 36 may present therapy adjustment information stored during a record mode of IMD 14, in which IMD 14 records posture state transitions, therapy adjustments, or other information, and even present nominal or suggested therapy parameters for a plurality of programs. This therapy adjustment information may be presented along with an indicator of the posture state of the patient in a playback mode. Patient 12 may then selectively set the plurality of programs to the respective nominal or suggested therapy parameters via a single confirmation input. As described herein, patient programmer 30 may be configured to perform any tasks described with respect to clinician programmer 60 or another external programmer 20. In addition, patient programmer 30 may accept input from patient 12 identifying symptoms such as pain or paresthesia that the patient recognizes during therapy or without any therapy being delivered.

Control pad 40 allows patient 12 to navigate through items displayed on display 36. Patient 12 may press control pad 40 on any of arrows 42, 44, 46, and 48 in order to move to another item on display 36 or move to another screen not currently shown on the display. In some embodiments, pressing the middle of control pad 40 may select any item highlighted in display 36. In other embodiments, scroll bars, a scroll wheel, individual buttons, or a joystick may perform the complete or partial functions of control pad 40. In alternative embodiments, control pad 40 may be a touch pad that allows patient 12 to move a cursor within the user interface displayed on display 36 to manage therapy.

Decrease button 50 and increase button 52 provide an input mechanism for patient 12. In general, decrease button 50 may decrease the value of a highlighted stimulation parameter every time the decrease button is pressed. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either of buttons 50 and 52 is selected, patient programmer 30 may initialize communication with IMD 14 or 26 to change therapy accordingly.

When depressed by patient 12, stimulation ON button 54 directs programmer 30 to generate a command for communication to IMD 14 that turns on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some embodiments, buttons 54 and 56 may be configured to perform operational functions related to stimulation therapy or the use of patient programmer 30. For example, buttons 54 and 56 may control the volume of audible sounds produced by patient programmer 30, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative embodiments, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative embodiments of patient programmer 30 may include other input mechanisms such as a keypad, microphone, camera lens, or any other media input that allows the user to interact with the user interface provided by patient programmer 30.

In alternative embodiments, the buttons of patient programmer 30 may perform different functions than the functions provided in FIG. 2 as an example. In addition, other embodiments of patient programmer 30 may include different button layouts or different numbers of buttons. For example, patient programmer 30 may even include a single touch screen that incorporates all user interface functionality with a limited set of buttons or no other buttons.

Figure 3:
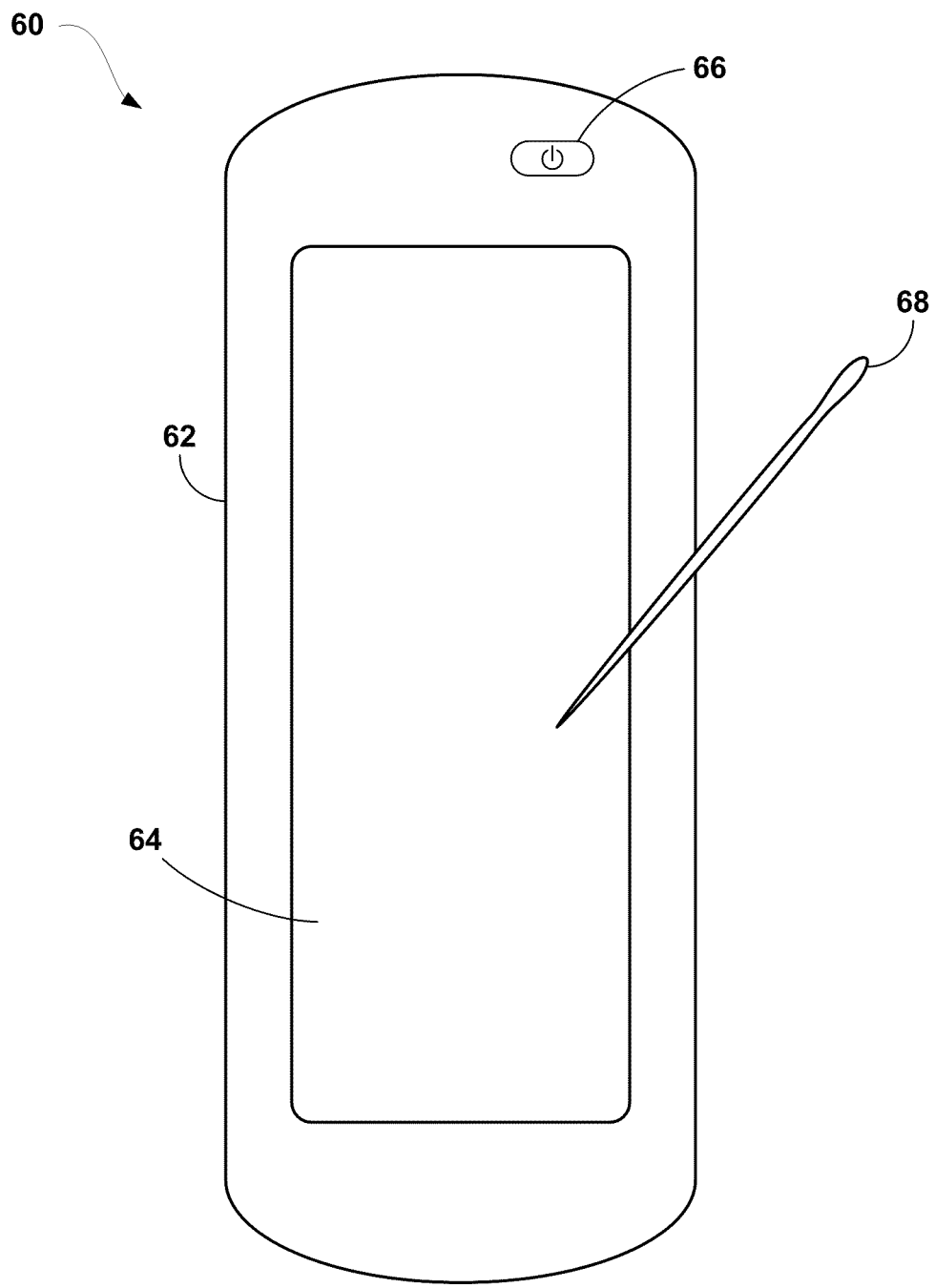
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by IMD 14. Clinician programmer 60 is a display device and an example embodiment of external programmer 20 illustrated in FIGS. 1A, 1B and 1C and may be used with either IMD 14 or IMD 26. In alternative embodiments, clinician programmer 60 may be used with an external medical device. As shown in FIG. 3, clinician programmer 60 provides a user interface (not shown) for a user, such as a clinician, physician, technician, or nurse, to manage and program stimulation therapy. As described herein clinician programmer 60 may be configured to display any of example user interfaces 200, 232, or 250 described herein. In this manner, clinician programmer may present one or more indicators of the posture state of patient 12, e.g., in or near real-time, based upon posture state data transmitted from IMD 14. Clinician programmer 60 is protected by housing 62, which encloses circuitry necessary for operation of clinician programmer 60.

Clinician programmer 60 is generally used by the clinician or other user to modify and review therapy to patient 12. The clinician may define each therapy parameter value for each of the programs that define stimulation therapy. The therapy parameters, such as amplitude, may be defined specifically for each of the posture states that patient 12 will be engaged in during therapy. The clinician may use clinician programmer 60 to calibrate, adjust, or define each posture state of patient 12 by using posture cones or other posture volumes as described herein or other techniques for associating posture state sensor output to the posture state of patient 12. Further, the clinician may use clinician programmer 60 to present an avatar or other indicator of a postures state of patient 12 based upon posture state data transmitted from IMD 14, e.g., in or near real-time. For example, programmer 60 may generate the appropriate anatomical configuration of the avatar to reflect a currently detected posture state and update this configuration as posture state data is transmitted from IMD 14.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some embodiments, the user may be able to touch display 64 with a finger, pen, or any other pointing device. In alternative embodiments, clinician programmer 60 may include one or more buttons, keypads, control pads, touch pads, or other devices that accept user input, similar to patient programmer 30.

In the illustrated embodiment, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some embodiments, clinician programmer 60 may be a larger device that may be less portable, such as a notebook computer, tablet computer, workstation, or even a remote computer that communicates with IMD 14 or 26 via a remote telemetry device to display example user interfaces 200, 232, or 250.

Most, if not all, of the functions of clinician programmer may be completed via the touch screen of display 64. The user may program stimulation therapy, modify programs or groups, retrieve stored therapy data, retrieve posture state information, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

In some cases, all processing may be performed in IMD 14 and distributed to clinician programmer 60 only for presentation to the clinician. Alternatively, two or more of IMD 14, clinician programmer 60, patient programmer 30, or another computing device may share in the processing duties of processing therapy adjustment information and any other data prior to presenting the information on clinician programmer 60. For example, IMD 14 may transmit posture state data that includes the raw sampled signal values generated by one or more sensors of the posture state module. Then programmer 60 may analyze this raw signal data according to a detection algorithm to identify the posture state of patient 12. As described above, in some examples, the identified posture state may be one or more of a real-time posture state, an asserted posture state, and a stable posture state. Alternatively, IMD 14 may perform the processing and analysis of the raw sampled signal values and then transmit the identified posture state(s) of patient 12 to programmer 60 or other external device. It should be noted that the processing and analysis of posture state data, including posture state sensor data, for example, for patient 12 could also be shared between the transmitting and receiving devices.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
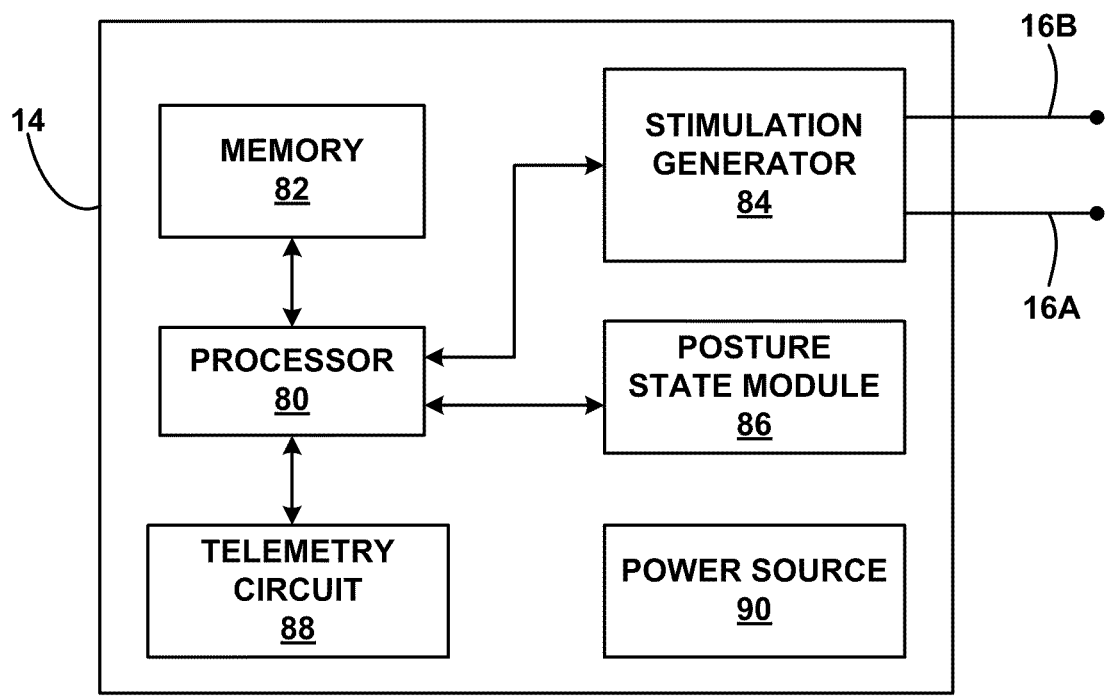
FIG. 4 is a functional block diagram illustrating various example components of an implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. Memory 82 may store instructions for execution by processor 80, stimulation therapy data, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information (including posture state data), program histories, and any other data that may benefit from separate physical memory modules.

Memory 82 may be considered, in some examples, a non-transitory computer-readable storage medium comprising instructions that cause one or more processors, such as, e.g., processor 80, to implement one or more of the example techniques described in this disclosure. The term "non-transitory" may indicate that the storage medium is not embodied in a carrier wave or a propagated signal. However, the term "non-transitory" should not be interpreted to mean that memory 82 is non-movable. As one example, memory 82 may be removed from IMD 14, and moved to another device. In certain examples, a non-transitory storage medium may store data that can, over time, change (e.g., in RAM).

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other embodiments, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode combination may be represented by a data stored in a memory location, e.g., in memory 82, of IMD 14. Processor 80 may access the memory location to determine the electrode combination and control stimulation generator 84 to deliver electrical stimulation via the indicated electrode combination. To change electrode combinations, amplitudes, pulse rates, or pulse widths, processor 80 may command stimulation generator 84 to make the appropriate change or changes to therapy according to instructions within memory 82 and rewrite the memory location to indicate the changed therapy. In other embodiments, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

In some examples, stimulation parameters or other therapy parameters may be adjusted to modify stimulation therapy delivered by IMD 14 based on the detected posture state of patient 12. In some examples, processor 80 may detect a posture state of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state to a stimulation program appropriate for patient's current posture state.

An exemplary range of electrical stimulation parameters likely to be effective in treating chronic pain, e.g., when applied to spinal cord 18, are listed below. However, other parameter values are contemplated. While stimulation pulses are described, stimulation signals may be of any of a variety of forms such as sine waves or the like.

Pulse Rate: between approximately 0.5 Hz and 1200 Hz, more preferably between approximately 5 Hz and 250 Hz, and still more preferably between approximately 30 Hz and 130 Hz.

Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications. Parameter values other than those described above are contemplated Processor 80 accesses stimulation parameters in memory 82, e.g., as programs and groups of programs. Upon selection of a particular program group, processor 80 may control stimulation generator 84 to deliver stimulation according to the programs in the groups, e.g., simultaneously or on a time-interleaved basis. A group may include a single program or multiple programs. As mentioned previously, each program may specify a set of stimulation therapy parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads.

Posture state module 86 allows IMD 14 to sense or detect a current patient posture state, e.g., posture, activity or any other static position or motion of patient 12. In the example of FIG. 4, posture state module 86 may include one or more accelerometers, such as three-axis accelerometers, or other sensor capable of detecting static orientation or vectors in three-dimensions. The three-axis accelerometer may be a micro-electro-mechanical accelerometer. In other examples, posture state module 86 may alternatively or additionally include one or more gyroscopes, pressure transducers or other sensors to sense the current posture state occupied by patient 12. Posture state information generated by posture state module 86 and processor 80 may correspond to an activity and/or posture undertaken by patient 12 or a gross level of physical activity, e.g., activity counts based on footfalls or the like.

Posture state data from posture state module 86 may be stored in memory 82 for later review by a clinician, used to adjust therapy, present one or more posture state indicators to patient 12, or some combination thereof. As an example, processor 80 may record the posture state parameter value (e.g., raw signal output) of the 3-axis accelerometer and assign the posture state parameter value to a certain predefined posture indicated by the posture state parameter value. In this manner, IMD 14 may be able to track how often patient 12 remains within a certain posture state. IMD 14 may also store which group or program was being used to deliver therapy when patient 12 was in the sensed posture. Further, processor 80 may also adjust therapy for a new posture state when posture state module 86 indicates that patient 12 has in fact changed posture states. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

A posture state parameter value from posture state module 86 that indicates the posture state may constantly vary throughout the day of patient 12. However, a certain activity (e.g., walking, running, or biking) or a posture (e.g., standing, sitting, or lying (front, back, left, right)) may include multiple posture state parameter values from posture state module 86. Memory 82 may include definitions for each posture state of patient 12. In one example, the detection algorithm for posture states may include definitions of each posture state may be illustrated as a cone in three-dimensional space. Whenever the posture state parameter value (e.g., a vector derived from sampled x, y, and z signal values) from the three-axis accelerometer of posture state module 86 resides within a predefined cone, volume or other zone, processor 80 indicates that patient 12 is in the posture state of the cone, volume, or other zone. In other examples, a posture state parameter value from the 3-axis accelerometer may be compared to values in a look-up table or equation to determine the posture state in which patient 12 currently resides.

Posture state responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 14 to, for example, depress one or more keys of patient programmer 30 multiple times during the patient posture state to maintain adequate symptom control. In some embodiments, patient 12 may eventually be able to enjoy posture state responsive stimulation therapy without the need to continue making changes for different postures via patient programmer 30. Instead, patient 12 may transition immediately or over time to fully automatic adjustments based on posture state.

As described above, the posture state of patient 12 detected by IMD 14 or other device based on posture state data from posture state module 86 may include a real-time posture state, an asserted posture state, and a stable posture state of patient. In some examples, IMD 14 may adjust therapy delivered to a patient upon a change in the stable posture state, for example, rather than a change in real-time posture state or asserted posture state. Indicators of two or more of such posture states may be displayed simultaneously in or near real-time on an external display device such as programmer 20, 30, or 60. In other examples, indicators of two or more of such patient posture states may be displayed simultaneously and on the same temporal basis on an external display but may reflect a historical review of patient posture states rather than a real-time representation.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional lead including a sensor positioned somewhere within patient 12, within an independent implantable sensor, or an accelerometer or other sensor externally worn on patient 12. In one example, one or more microsensors may be implanted within patient 12 or externally worn to communicate posture state information wirelessly to IMD 14 or other device. In this manner, a posture state of patient 12 may be determined from multiple activity sensors placed at various locations on or within the body of patient 12.

In some examples, processor 80 processes the analog output of the posture state sensor in posture state module 86 to determine activity and/or posture data. For example, where the posture state sensor comprises an accelerometer, processor 80 or a processor of posture state module 86 may process the raw sensor signals provided by the posture state sensor to determine activity counts. In some embodiments, processor 80 may process the sensor signals provided by the posture state sensor to determine velocity of motion information along each axis.

In one example, each of the x, y, and z signals provided by the posture state sensor has both a DC component and an AC component. The DC components may describe the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient. The AC component of the x, y and z signals may yield information about patient motion. In particular, the AC component of a signal may be used to derive a value for an activity describing the patient's motion. This activity may involve a level, direction of motion, or acceleration of the patient.

One method for determining the activity is an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count."

The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined as describing a direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

In other embodiments, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

Posture state module 86 may sample output of the postures state sensor(s) at any sample rate suitable for therapy or desired to present one or more posture state indicators in or near real-time via an external display. The sample rate may indicate how often processor 80 samples the output of the posture state sensor signals of posture state module 86. In some examples, output of the posture state sensor of posture state module 86 is sampled at a sample rate between about 1 Hz and about 60 Hz, such as, e.g., between about 10 Hz and about 40 Hz. However, the sample rate may be any slower or faster rate supported by the processing capabilities of IMD 14 circuitry. In some examples, it may be beneficial to sample at the slowest rate needed for effective posture state detection to conserve battery life.

Wireless telemetry in IMD 14 with external programmer 20 or other display device, e.g., patient programmer 30 or clinician programmer 60, or another device may be accomplished by radio frequency (RF) communication or proximal inductive interaction of IMD 14 with external programmer 20. In some examples, telemetry circuit 88 may support Bluetooth-based communication between IMD 14 and external programmer 20 or other external device. Telemetry circuit 88 may send information to and receive information from external programmer 20, on a continuous basis, at periodic intervals, at non-periodic intervals, or upon request from the stimulator or programmer.

Processor 80 controls telemetry circuit 88 to send and receive information to and from external programmer 20. For example, processor 80 commands telemetry circuit 88 to transmit information, e.g., posture state data, in or near real-time when communicating to any external display device. For posture state data transmitted in or near real-time, telemetry circuit 88 may send the most recently detected posture state (s) or sampled sensor signal values, or a rolling average posture state and/or sample sensor signal values at or near the fasted rate supported by the telemetry circuit. The posture state data may be transmitted to an external device at a rate between about every two seconds and about ten times per second, such as, e.g., between about every second and about three time per second. Other posture state data transmission rates are contemplated. However, processor 80 may transmit posture state data via telemetry circuit 88 at a slower or faster rate depending upon the requirements of the user viewing the real-time display of patient posture state and the display capabilities of the display device, e.g., the rate at which the display may be refreshed.

In some examples, the posture state data may be transmitted from IMD 14 to external programmer 20 or other display device at a rate substantially the same as the rate processor 80 samples the posture sensor signal of posture state module 86. In other examples, the posture state data may be transmitted from IMD 14 to external programmer 20 or other external display device at rate that is less than the sensor sampling rate. In such case, the posture sensor data transmitted from IMD 14 to the external display device may include information regarding only a single sampled sensor value or a plurality of sensor values, e.g., those sensor values sampled since the prior transmission to the external device. To support RF communication, telemetry circuit 88 may include appropriate electronic components, such as amplifiers, filters, mixers, encoders, decoders, and the like. In some examples, the rate at which the posture state data is transmitted from IMD 14 to external programmer 20 or other display device may depend on the graphic capability of the display device (e.g., rate at which graphical representations may be updated on a display screen), rate of patient movement (e.g., the rate at which patient 12 may be able to physically change posture states), and/or the sampling rate of the posture state sensor of IMD 14.

In non-continuous transmission applications, processor 80 may control the transmission of posture state data differently. For example, when processor 80 determines that patient 12 has changed to a different posture state via posture state module 86, processor 80 may communicate with patient programmer 30 via telemetry circuitry 88 to indicate the newly detected posture state currently occupied by patient 12. In this manner, processor 80 may force patient programmer 30 to present a different posture state indication based upon the sensed posture state parameter value of the patient posture state. In particular, processor 80 may transmit a new posture state detection to patient programmer 30 to indicate the currently detected posture state occupied by the patient. Alternatively, processor 80 may periodically or non-periodically send posture state information to patient programmer 30 either unilaterally or in response to a request from patient programmer 30. For example, patient programmer 30 may request the posture state parameter value or currently detected posture state, either of which indicates detected posture state, and independently change the posture state indication when it is appropriate to do so.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, rechargeable or non-rechargeable batteries may be used for a limited period of time. As a further alternative, an external inductive power supply could transcutaneously power IMD 14 when needed or desired.

Figure 5:
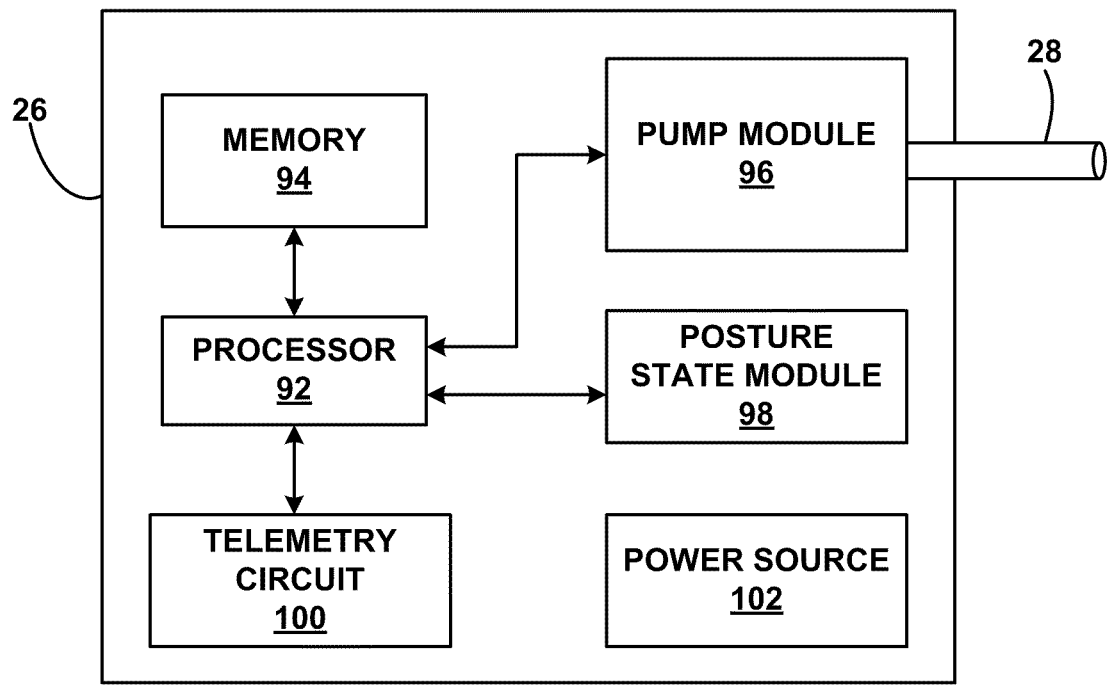
FIG. 5 is a functional block diagram illustrating various example components of an implantable drug pump.

FIG. 5 is a functional block diagram illustrating various components of an IMD 26 that is a drug pump. IMD 26 is a drug pump that operates substantially similar to IMD 14 of FIG. 4. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 may control pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts their posture.

Figure 6:
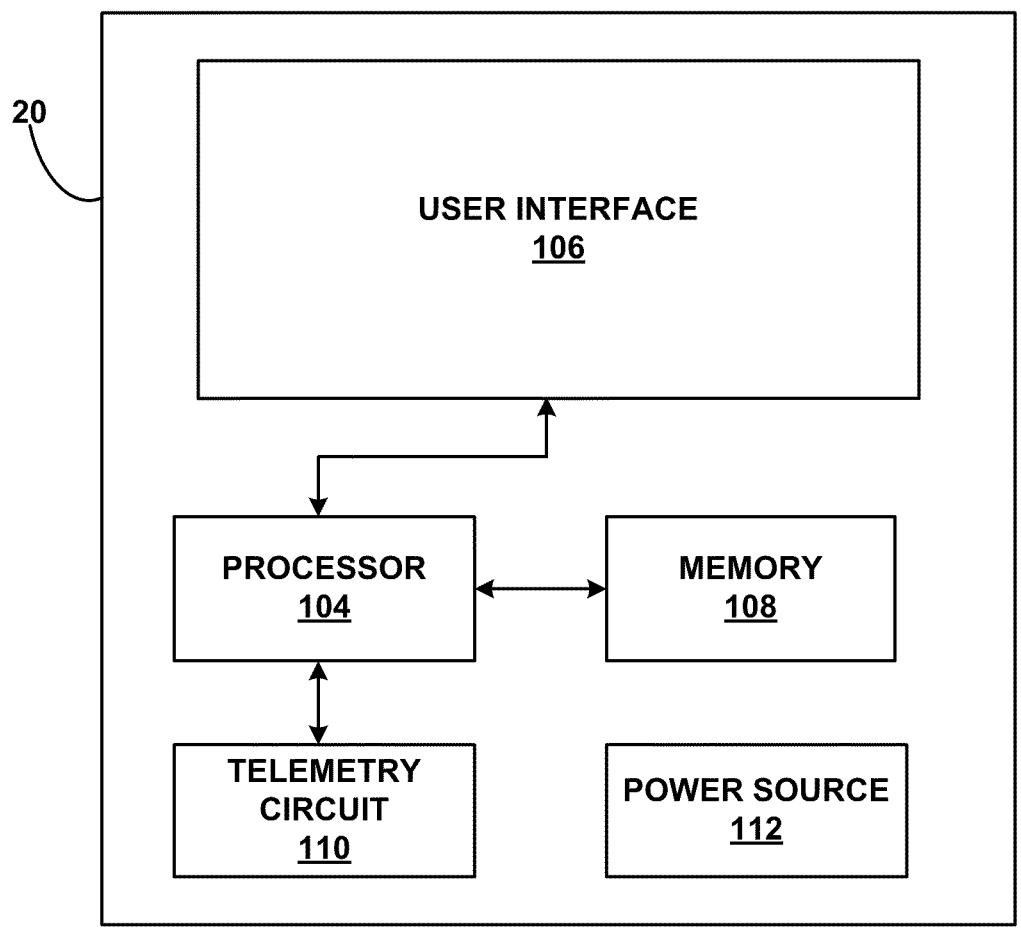
FIG. 6 is a functional block diagram illustrating various example components of an external programmer for an implantable medical device.

FIG. 6 is a functional block diagram illustrating various components of an external programmer 20 for IMDs 14 or 26. As shown in FIG. 6, external programmer 20 is an external display device that includes processor 104, memory 108, telemetry circuit 110, user interface 106, and power source 112. External programmer 20 may be embodied as patient programmer 30 or clinician programmer 60. A clinician or patient 12 interacts with user interface 106 in order to manually change the stimulation parameters of a program, change programs within a group, turn posture responsive stimulation ON or OFF, view therapy information, view posture state information, view an avatar or other indicator(s) of patient postures state in or near real-time, or otherwise communicate with IMDs 14 or 26.

User interface 106 may include a screen or display and one or more input buttons, as in the example of patient programmer 30, that allow external programmer 20 to receive input from a user. Alternatively, user interface 106 may additionally or only utilize a touch screen display, as in the example of clinician programmer 60. As described herein, user interface may be embodied as example user interfaces 200, 232, or 250. The screen may be a liquid crystal display (LCD), dot matrix display, organic light-emitting diode (OLED) display, touch screen, or any other device capable of delivering and/or accepting information. For an avatar posture state indicator or other visible posture state indicators, a display screen may suffice. For audible and/or tactile posture state indicators, programmer 20 may further include one or more audio speakers, voice synthesizer chips, piezoelectric buzzers, or the like.

Input buttons for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

Telemetry circuit 110 allows the transfer of data to and from IMD 14, or IMD 26. When presenting the avatar in real-time, telemetry circuit 110 may communicate automatically with IMD 14 in or near real-time. Telemetry circuit 110 may receive the posture state data from IMD 14 or 26 in or near real-time, and immediately send the posture state data to processor 104 for any analysis before processor 104 generates and presents one or more posture state indicators based on the received posture state data on user interface 106.

In addition, telemetry circuit 110 may communicate at a scheduled time or when the telemetry circuit detects the proximity of the stimulator. User interface 106 may then update displayed information accordingly. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMD 14. In other cases, the programmer may be integrated with a recharging functionality in the combined programming/recharging device. The techniques described herein may be communicated between IMD 14 via any type of external device capable of communication with IMD 14.

Processor 104 may also analyze the posture state data transmitted, e.g., in or near real-time, from IMD 14 when the transmitted posture state data is the raw posture sensor signal from the posture state module. Processor 104 may utilize the same detection algorithm(s) of IMD 14 to identify the posture state of patient 12 from the raw or unprocessed posture state data. Alternatively, processor 104 may use an alternative detection algorithm as requested by the user. If the real-time indicator or other posture state indicator presented by external programmer 20 is not correlating with actual patient 12 posture states, the user may desire to use a different detection algorithm that may more accurately identify the patient posture state. In this manner, processor 104 may toggle between different detection algorithms as requested by the user. If a different detection algorithm is selected for use, processor 104 may transmit the new algorithm to IMD 14 or 26 for use during therapy.

Figure 7:
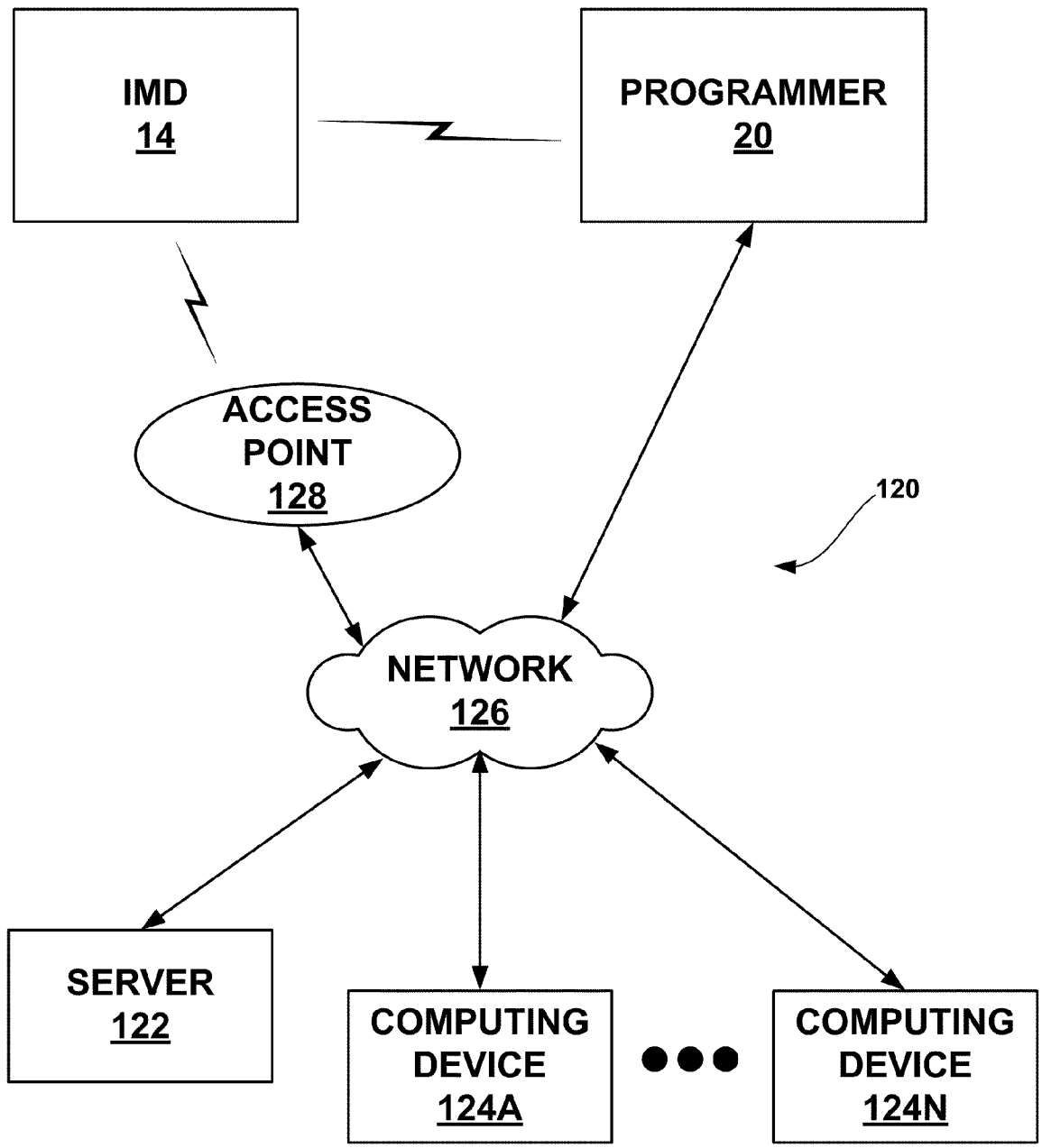
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the patient 12 posture state, such as what percentage of time patient 12 was in each identified posture. In other cases, however, IMD 14 may send stored data relating to posture state information to external programmer 20 and/or server 122, either wirelessly or via access point 128 and network 126, for remote processing and analysis.

For example, IMD 14 may sense, process, trend and evaluate the sensed posture state information, including posture state data. This communication may occur in or near real-time, and network 126 may allow a remote clinician to review the current patient posture state by receiving a presentation of posture state indicator(s) along with other therapy information on a remote display device, e.g., computing device 124A. For example, the remote clinician may view a real-time posture state indicator of patient 12 or indicator of other identified patient posture state in a location separate to that of patient 12. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review the historical therapy information including the stimulation parameters, symptoms, and posture states to possibly identify any problems or issues with the therapy that should be addressed.

In addition, network 126 may be configured to facilitate substantially real-time communication between IMD 14 and computing device 124A for programming with the current posture state of the patient. Although there may be some slight time delay in the transfer of information, this may still be considered real-time programming utilizing any user interface such as user interfaces 200, 232, or 250. The clinician may be able to remotely visit with patient 12, review stored therapy information, and make any programming changes, e.g., in or near real-time, using system 120.

In some cases, server 122 may be configured to provide a secure storage site for archival of posture state information that has been collected from IMD 14 and/or external programmer 20. Network 126 may comprise a local area network, wide area network, or global network, such as the Internet. In other cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients. Further, posture state detection may also be used to provide notifications, such as providing notification via a wireless link to a care giver that a patient has potentially experienced a fall.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs or external medical devices that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
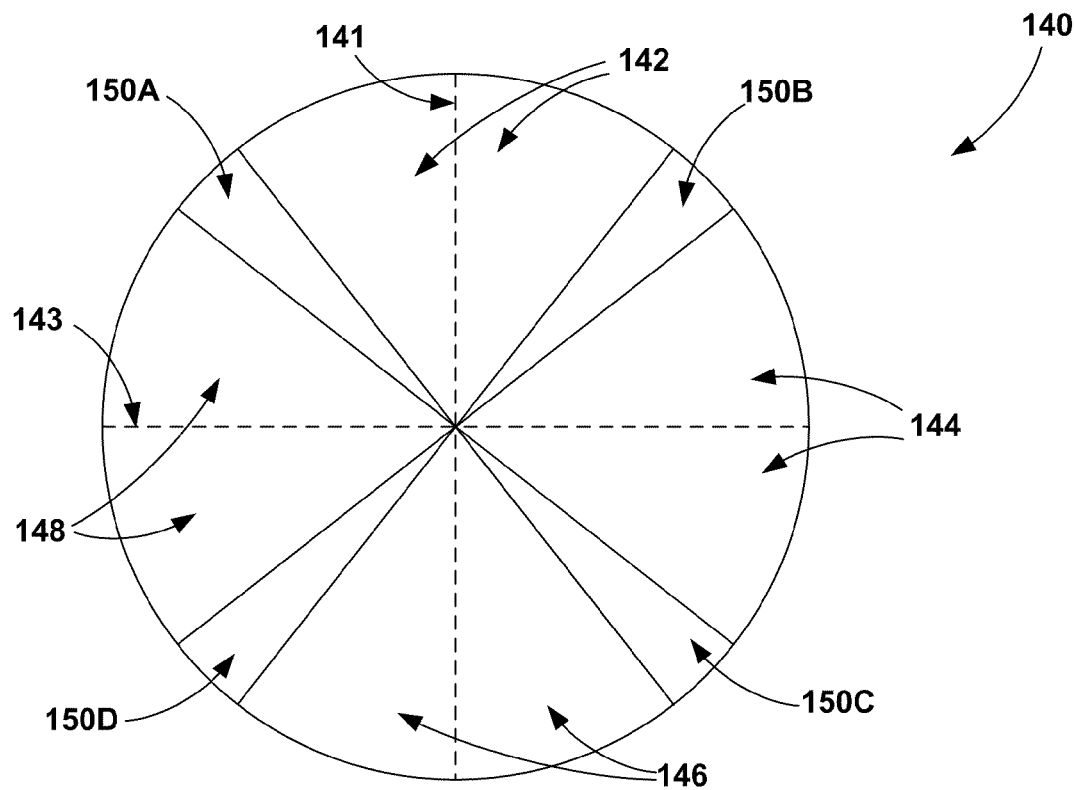
FIGS. 8A-8C are conceptual illustrations of posture cones that may be used to define a posture state of a patient based on signals sensed by a posture state sensor, in one example.
Figure 8B:
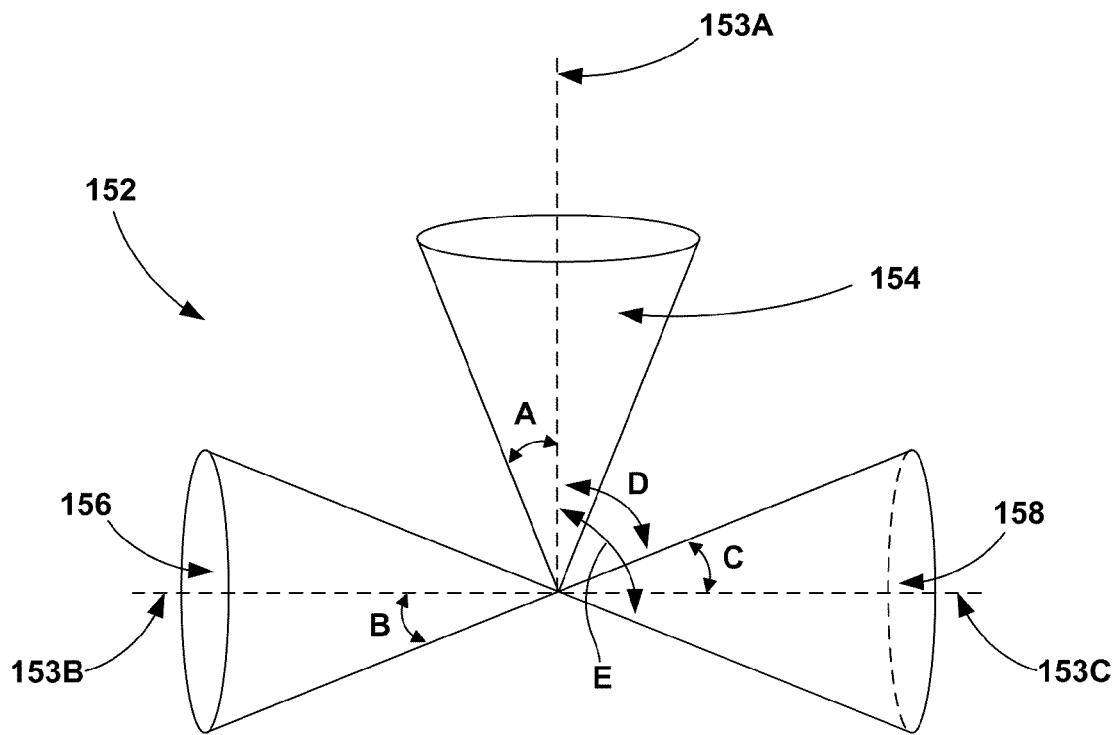
Figure 8C:
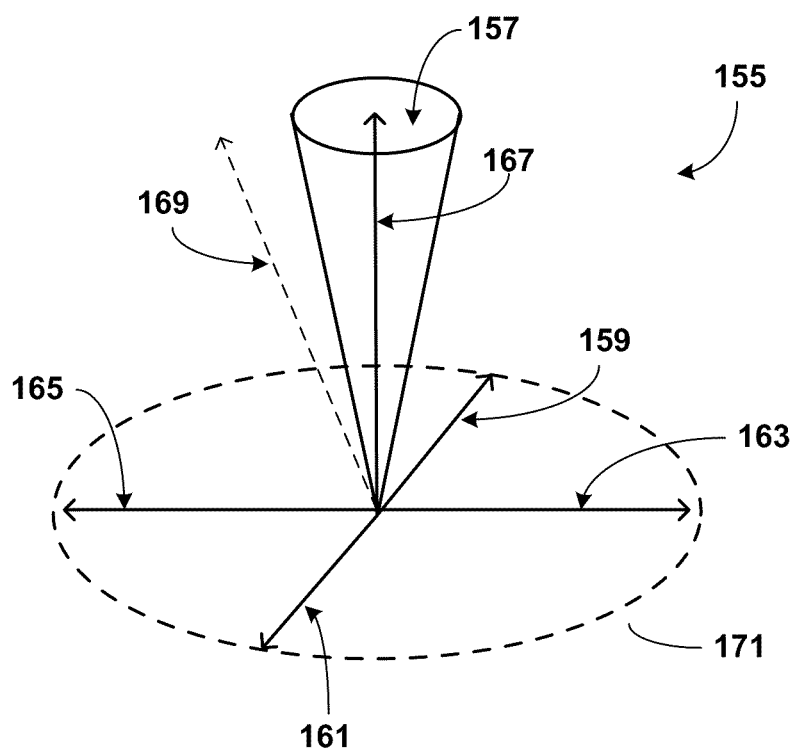

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 or processor 80, for example, with respect to posture state spaces 140, 152, 155 to determine the posture state of patient 12. For example, if the output of one or more posture state sensors is within a particular posture state region defined by posture state reference data, posture state module 86 may determine that patient 12 is within the posture state associated with the respective posture state region. Spaces 140, 152, and 155 may be altered to represent different detection algorithms used to identify the posture state of patient 12 from the raw posture state parameter values (e.g., sample posture sensor signal values). Alternatively, the difference spaces 140, 152, and 155 may each represent different detection algorithms that the user may select for system 10 use in identifying the posture state of patient 12.

In some cases, one or more posture state regions may be defined as posture state cones. Posture state cones may be used to define a posture state of patient 12 based on the output from a posture state sensor of a posture state module according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state module, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value, e.g., a sample sensor signal value, from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone may be positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Moreover, the reference coordinate vectors need not reside in the same plane. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture state information as a determined posture state or as raw output from the posture state sensor, change therapy according to the posture, or both. Additionally, IMD 14 may communicate the posture state information to patient programmer 30 so that the patient programmer can present a posture state indication to patient 12, e, g., via programmer 20.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A.

The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other, and need not even reside within the same plane. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another, and need not reside within a same plane.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E' may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above.

In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167.

Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

As will be described further below, in response to the presentation of one or more posture state indicators presented on programmer 20 in or near real-time as described in some examples herein, the user may desire to adjust any of the cones of spaces 140, 150, and 155, or other posture zones used to define the posture state of patient 12 based on the output of one or more posture sensors. For example, if one or more of the posture state indicators presented does not match the actual posture state of patient 12, the user may desire to adjust the detection algorithms that identify patient posture state. The user may perform this re-calibration or adjustment of the posture state module at any time, and once performed, the avatar may reflect the changes. One or more example techniques for reorienting IMD 14 or other medical device may be described in U.S. patent application Ser. No. 12/433,623, titled "REORIENTATION OF PATIENT POSTURE STATES FOR POSTURE-RESPONSIVE THERAPY," filed Apr. 30, 2009, the entire content of which is incorporated by reference herein.

Figure 9:
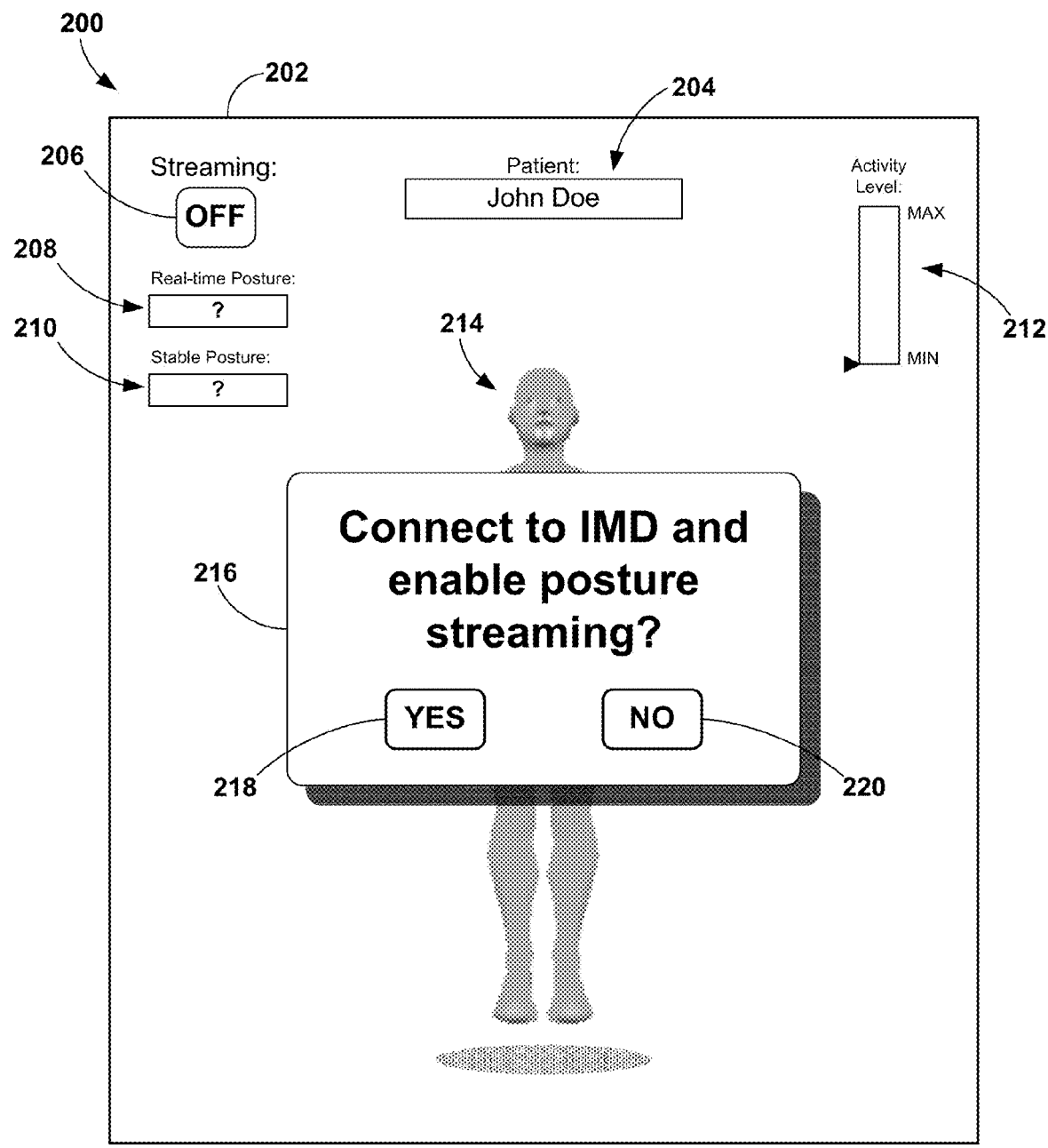
FIG. 9 is a conceptual diagram illustrating an example user interface for displaying a connection prompt for transmitted posture state data.

FIG. 9 is a conceptual diagram illustrating an example user interface 200 for displaying a connection prompt 216 before real-time streaming or other transmission of posture state data from an IMD to an external display device. Real-time streaming of postures state data is one example technique for transferring data in a manner that may allow an external display device to present one or more indicators that reflects the posture state of a patient in or near real-time based on posture state data received from a medical device. For ease of description, the transfer of posture state data is referred to in some instances as being streamed or streamed in or near real-time. However, as described above, examples of the disclosure may not be limited to the transfer of posture state data via real-time streaming from IMD 14, 26 or other medical device to an external display device. Compared to that of non-real time transfer of posture state data, the transfer of posture state data from IMD 14 to external programming device 20 in or near real-time may allow one or more indicators of patient posture state to substantially mirror the actual movement of patient 12 as it occurs and/or is sensed by posture state module 86.

As shown in FIG. 9, user interface 200 provides screen 202 that includes data streaming indicator 206, real-time posture state text 208, stable posture state text 210, patient indicator 204, activity level 212, and avatar 214. Data streaming indicator 206 displays the word "OFF" to indicate that posture state data is not being streamed to the external display device at this time. User interface 200 may be included on any external display device, such as programmer 20, 30, or 60. In general, user interface 200 will be described in regard to programmer 20 and IMD 14, but system 10 may include any programmer, display device, and medical device described herein. The medical device may be an external device or implantable device. The medical device may or may not be configured to deliver therapy to a patient.

Before user interface 200 begins to present substantially real-time information to the user, screen 202 provides a pop-up window of connection prompt 216. Once the user has indicated that a real-time indicators of patient posture state are to be presented by programmer 20, user interface 200 displays connection prompt 216 to ensure that real-time streaming of posture state data (or other transfer of posture state data in accordance with examples of the disclosure) from IMD 14 or 26 should commence. If the user selects no button 220, user interface 200 returns to the previous menu or a main menu. If the user selects yes button 218, user interface 200 instructs processor 104 of programmer 20 to communicate with IMD 14 that real-time streaming of posture state data should commence. In other examples, connection prompt 216 may allow the user to specify details about the real-time streaming of posture state data (e.g., the particular rate at which postures state data is transferred from IMD 14 to programmer 20).

FIGS. 10-14 are conceptual diagrams illustrating example screens 222, 224, 226, 228, and 230 of user interface 200 for displaying avatar 214 and other posture state indicators 208, 209, 210 based on posture state data for patient 12. In addition to real-time posture state text 208 and stable posture state text 210 shown in example screen 202, screens 222, 224, 226, 228, and 230 include asserted posture state text 209. Real-time posture state indicator 208 reflects the real-time posture state of patient 12 identified using real-time posture state detection criteria. Asserted posture state text 209 reflects the asserted posture state of patient 12 identified using asserted posture state detection criteria. Stable posture state text 210 reflects the stable posture state of patient 12 identified using the stable posture state detection criteria. In some examples, the detection criteria for respective posture states may include unique detection algorithms used to process posture state data (e.g., one or more accelerometer signals) to detect the posture state of patient 12. In this manner, different detection algorithms may be used to define each of asserted, stable, and real-time posture states.

Avatar 214 may be displayed by user interface 200 in different anatomical configurations to graphically represent the posture state of patient 12 which is updated in or near real-time in relation to the actual posture state of patient 12. In the examples shown in FIG. 10-14, avatar 214 corresponds to the real-time posture state of patient 12, which is also indicated by real-time posture state indicator text 208. However, in some examples, avatar 214 may indicate a posture state of patient 12 other than that of the real-time posture state of patient 12.

In some examples, the posture state indicated by avatar 214 and real-time text 208 displayed on user interface 200 may change substantially simultaneously with changes in the actual posture state of patient 12. In cases in which the real-time posture state data reflects the posture state of patient 12 computed according to the each sampled set of posture state sensor values (e.g., sampled values for x, y, and z signals), user interface 200 may update avatar 214 and real-time posture state indicator text 208 at a rate substantially the same as the signal sampling rate.

Figure 10:
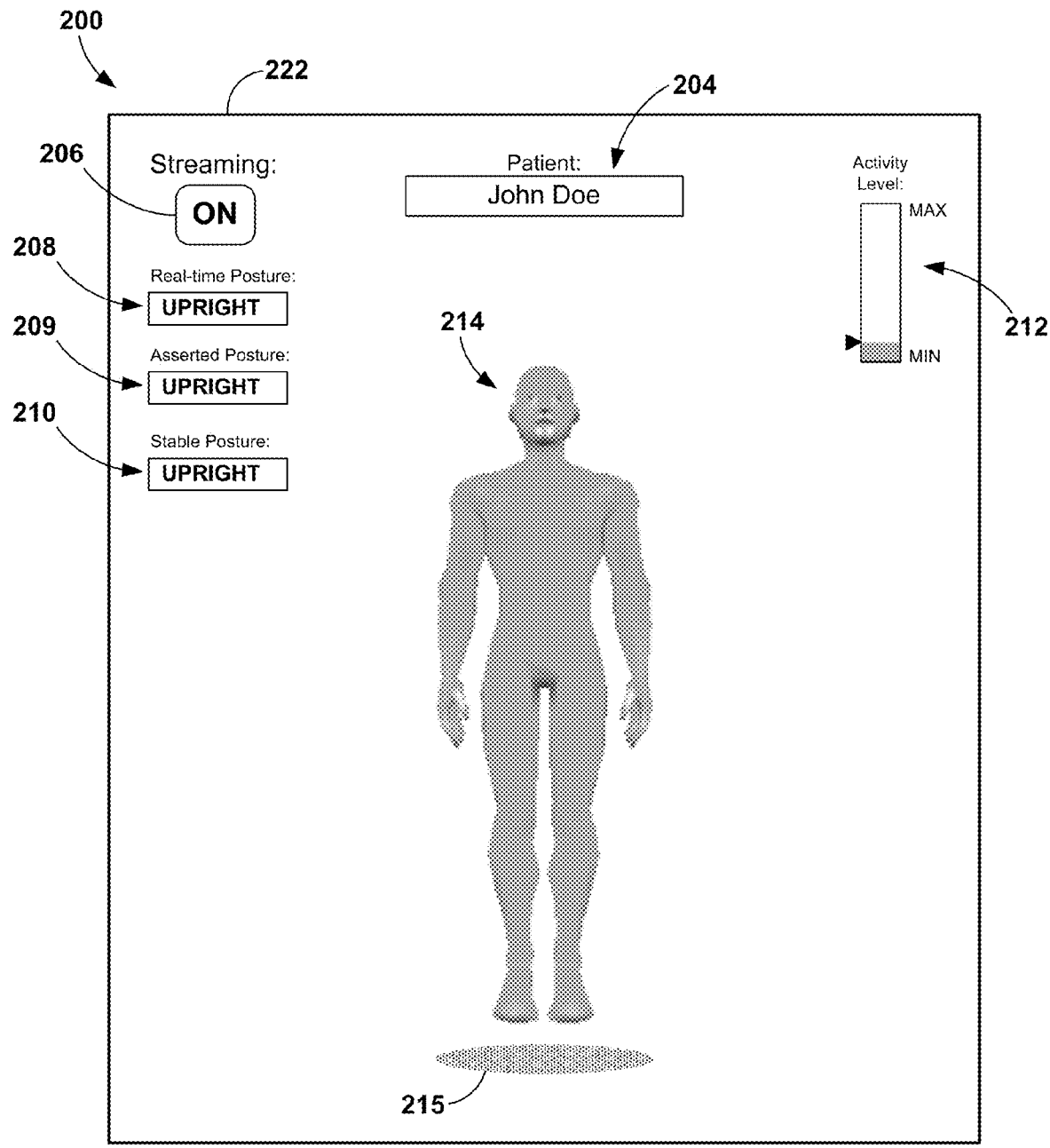
FIGS. 10-14 are conceptual diagrams illustrating example screens of a user interface for displaying an example posture state indicator for a patient based on posture state data.

As shown in FIG. 10, user interface 200 provides screen 222 that includes streaming indicator 206, real-time posture text 208, asserted posture state text 209, stable posture text 210, patient indicator 204, activity level 212, avatar 214 and ground indicator 215. Streaming indicator 206 displays the word "ON" to indicate that posture state data is being streamed in real-time and that avatar 214 is reflecting the real-time posture state of patient 12.

Avatar 214 is a graphical representation of the posture state of the patient and is presented in an anatomical configuration based upon the posture state data transmitted, e.g., streamed, from IMD 14 in or near real-time. Here, avatar 214 is shown in the upright or standing posture state. Ground indicator 215 is shown as a shadow of avatar 14 to indicate to the user the direction of gravity. In other examples, ground indicator 215 may not be utilized.

Although avatar 214 is shown as a generic grey human model, avatar 214 may be any type of graphical representation of a human form. For example, avatar 214 may be generated from a picture or medical image of patient 12 so that the avatar looks very similar to patient 12. In other examples, avatar 214 may be a more simplistic human representation useful for visually indicating the posture state of patient to a user determined based on the received posture state data. Simplistic representations may include block segments of extremities, stick figures, or other generic shapes. User interface 200 may allow the user to change avatar 214 to a different form or use different patient information as desired. Additionally or alternatively, avatar 214 may be modified to indicate one or more other physiological parameters of patient 12. For example, avatar 214 may change color depending upon the heart rate or temperature of patient 12. Avatar 214 is one example of a visual representation of patient posture state that may be present to a user via user interface 200 of external programmer 20. Other visual representations of patient posture state are contemplated. In some examples, non-visual representations may be additionally or alternatively presented to a user via user interface 200 to indicate a detected patient posture state.

Avatar 214 may be shown in any anatomical configuration that represents the posture state of patient 12. Example anatomical configurations of avatar 214 include an upright configuration, a reclining configuration, a lying back configuration, a lying front configuration, a lying left configuration, a lying right configuration, a walking configuration, a running configuration, and a biking configuration. In some examples, avatar 214 may be capable representing any patient posture state detectable by IMD 14 via postures state module 86. Although changes in avatar 214 configurations may be between discrete posture states, alternative examples of user interface 200 may provide an animated avatar that moves with patient 12 in or near real-time. In some examples, avatar 214 may be oriented to reflect the particular sensed vector coordinates derived from sample sensor signals. For example, the sensed vector coordinate may be computed from a sampled set of x, y, and z signal values. In this manner, avatar 214 may provide a representation of patient 14 configuration that not only indicates the real-time patient posture state, but also a more precise position within the real-time patient posture state. An example of such a case is illustrated further in FIGS. 16A and 16B.

Real-time posture state text 208, asserted posture state text 209, and stable posture state text 210 are visual posture state indicators that supplement the presentation of avatar 214. Real-time posture text 208 substantially mirrors the anatomical configuration represented by avatar 214 by providing a textual indication of the current real-time posture state of patient according to the posture state data received from IMD 14. Although indicators for each of real-time posture state, asserted posture state, and stable posture state are concurrently display on screen 222, other examples are contemplated with one, two, or more than two of real-time posture state, asserted posture state, stable posture state or the like are selectively indicated by screen 222.

Similar to real-time posture text 208, asserted posture state text 209 and/or stable posture text 210 may mirror the anatomical configuration represented by avatar 214 even though avatar 214 is indicative of the real-time posture state of patient 12. However, asserted posture state text 209 and stable posture text 210 may not always mirror avatar 214 and real-time posture state text 208.

As described above, stable posture text 210 may indicate the posture state currently used by IMD 14, for example, to deliver therapy to patient 12, based on the result of a detection algorithm, and is not necessarily the current or real-time posture state occupied by patient 12 based on recently sample sensor signal values. Since patient 12 may move between two or more posture states in a relatively short period of time, patient 12 may not benefit from the relatively fast changes in therapy parameters that could accompany such movement if the therapy was changed for every posture state occupied by patient 12. As such, in some examples, only when patient 12 is within a single posture state for a predetermined period of time does IMD 14 recognize the posture state as stable for changing therapy according to the detected patient posture state. In some cases, the predetermined amount of time may be referred to as a "dwell time." Therefore, stable posture text 210 may be equal to real-time posture text 208 only after patient 12 occupies the real-time posture state for the dwell time. Similarly, in some examples, patient 12 may occupy the same asserted posture state for a dwell time for that posture state to also be considered the stable posture state of patient 12.

By displaying stable posture text 210 concurrently with avatar 214 and real-time posture text 208 on the same temporal basis, a user may be able to gauge the amount of time that patient 12 must occupy a posture state prior to IMD 14 adjusting the therapy delivered to patient. In some examples, a user may set and/or adjust one or more posture state dwell times for patient 12 based at least in part on the "real-time" display of the stable posture of patient 12 relative avatar 214, when avatar 214 is representative of real-time posture state.

In a similar fashion, by displaying asserted posture state text 209 concurrently with avatar 214 and real-time posture state text 208 on the same temporal basis, a user may be able to gauge the amount of time between a user occupying a real-time posture state prior to the posture state also being detected as an asserted posture state. Furthermore, a user may be able to gauge the number of occurrences that the real-time posture state of patient 12 is different from that of the asserted posture state of patient 12, e.g., while still maintaining the same asserted posture state. In this manner, a user may be able to evaluate the performance of one or more posture state detection algorithms for detecting a patient posture state. In particular, in the case when the asserted posture state of patient 12 lags behind the real-time posture state of patient 12 for an undesirable length of time, a user may adjust the sampling algorithm (e.g., M of N filter algorithm) used to detect the asserted posture state of patient 12.

Activity level 212 displays the activity of patient 12 as indicated by the activity count from posture state module 86. When activity level 212 is low, patient 12 is relatively stationary and not accelerating in any direction, as shown in screen 222. If activity level 212 is high, patient 12 is moving actively. In other examples, activity level 212 may provide the actual activity count data generated by posture state module 86 instead of, or in addition to, the graph of activity level 212.

In some examples of user interface 200, the user may be able to toggle between different posture state detection algorithms. For example, if a clinician determines that real-time avatar 214 or asserted posture state text 209 is not accurately representing the current posture state actually engaged by patient 12 and/or actual changes between patient posture state, the clinician may desire to change the manner in which IMD 14 identifies the posture state of patient 12 from the sampled signal values of the one or more accelerometers of posture state module 86. Once the clinician has toggled to a desired detection algorithm, IMD 14 may be commanded via programmer to set the new algorithm for use during therapy delivered by IMD 14. In some examples, a new posture state detection algorithm may be trialed on user interface 200 using avatar 214, for example, prior to or concurrently with the implementation of the posture state detection algorithm for user during therapy delivered to patient 12 via IMD 14.

Figure 11:
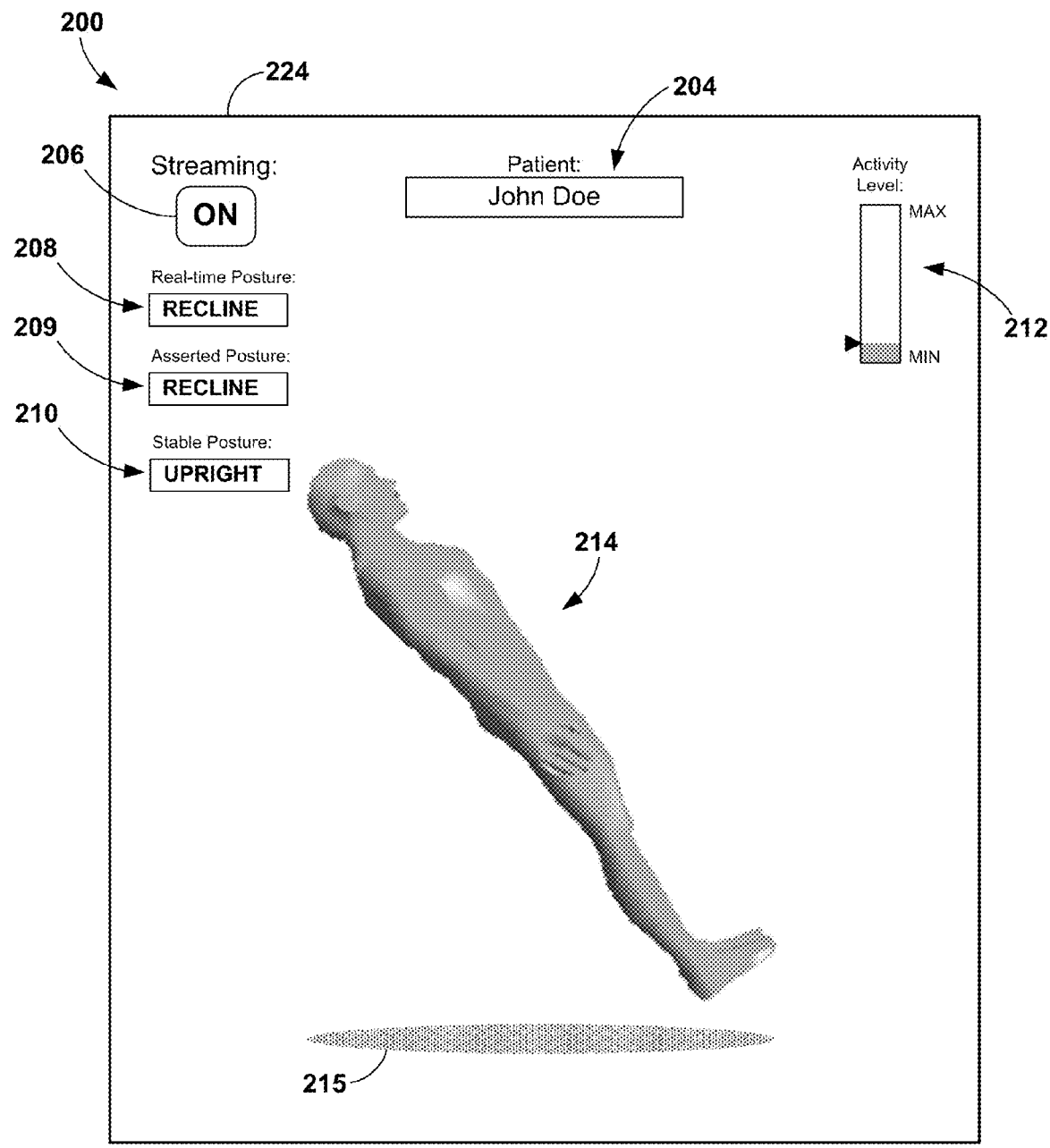

As shown in FIG. 11, user interface 200 presents screen 224. Posture state data streamed (or otherwise transmitted) from IMD 14 in or near real-time to programmer 20 indicates that patient 12 has changed posture states from screen 222. In particular, the posture state data received by programmer 20 indicates that the postures state of patient 12 has changed from a standing posture state to a reclined posture state for each of real-time and asserted postures states. In return, processor 104 (FIG. 6) generates and presents avatar 214 in a reclined anatomical configuration to represent the current "reclined" posture state of patient 12. Real-time posture text 208 and asserted posture text 209 indicate that patient 12 is currently occupying the "recline" posture state.

However, as the posture state data received by programmer 20 indicates that the stable posture state of patient 12 has not yet changed to the "recline" posture state but instead remains in the "upright" posture state. This may be the case, for example, if the real-time and/or asserted posture state of patient 12 has not been in the "recline" posture state for the dwell time associated with the posture state or posture state transition. Instead, patient 12 may have only recently transitioned to the "recline" posture state from the "upright" posture state and has not occupied the "recline" posture state for longer than the predefined dwell time.

Figure 12:
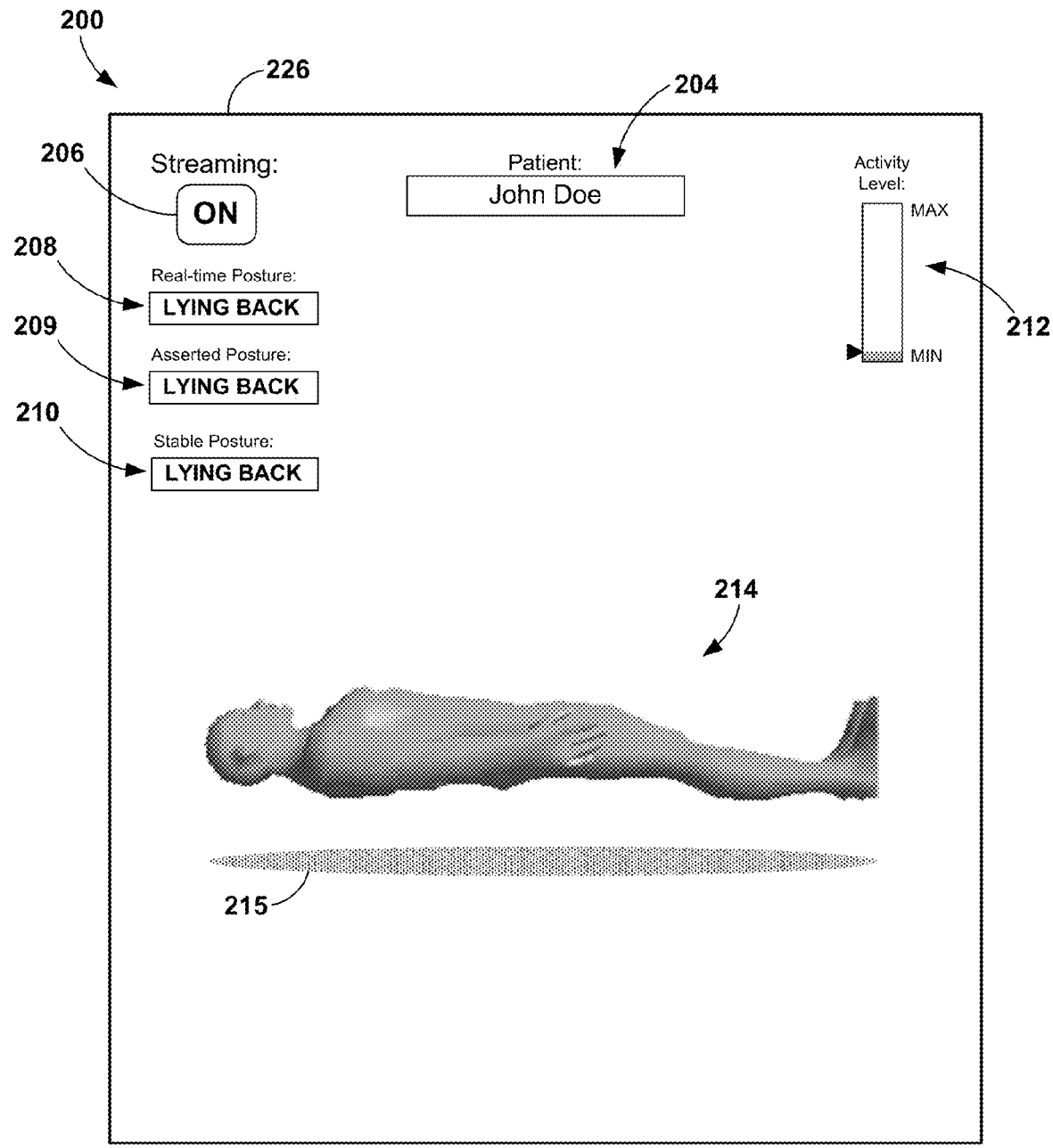

As shown in FIG. 12, screen 226 of user interface 200 indicates that the posture state data streamed (or otherwise transmitted) from IMD 14 has caused user interface 200 to generate and present avatar 214 in a lying back anatomical configuration to represent a current "lying back" posture state for patient 12 for each of the real-time, asserted and stable posture states. The lying back avatar 214 in FIG. 12 is also supplemented by real-time posture text 208, asserted posture state text 209 and stable posture state text 210 each indicating that patient 12 is currently engaged in the "lying back" posture state.

Figure 13:
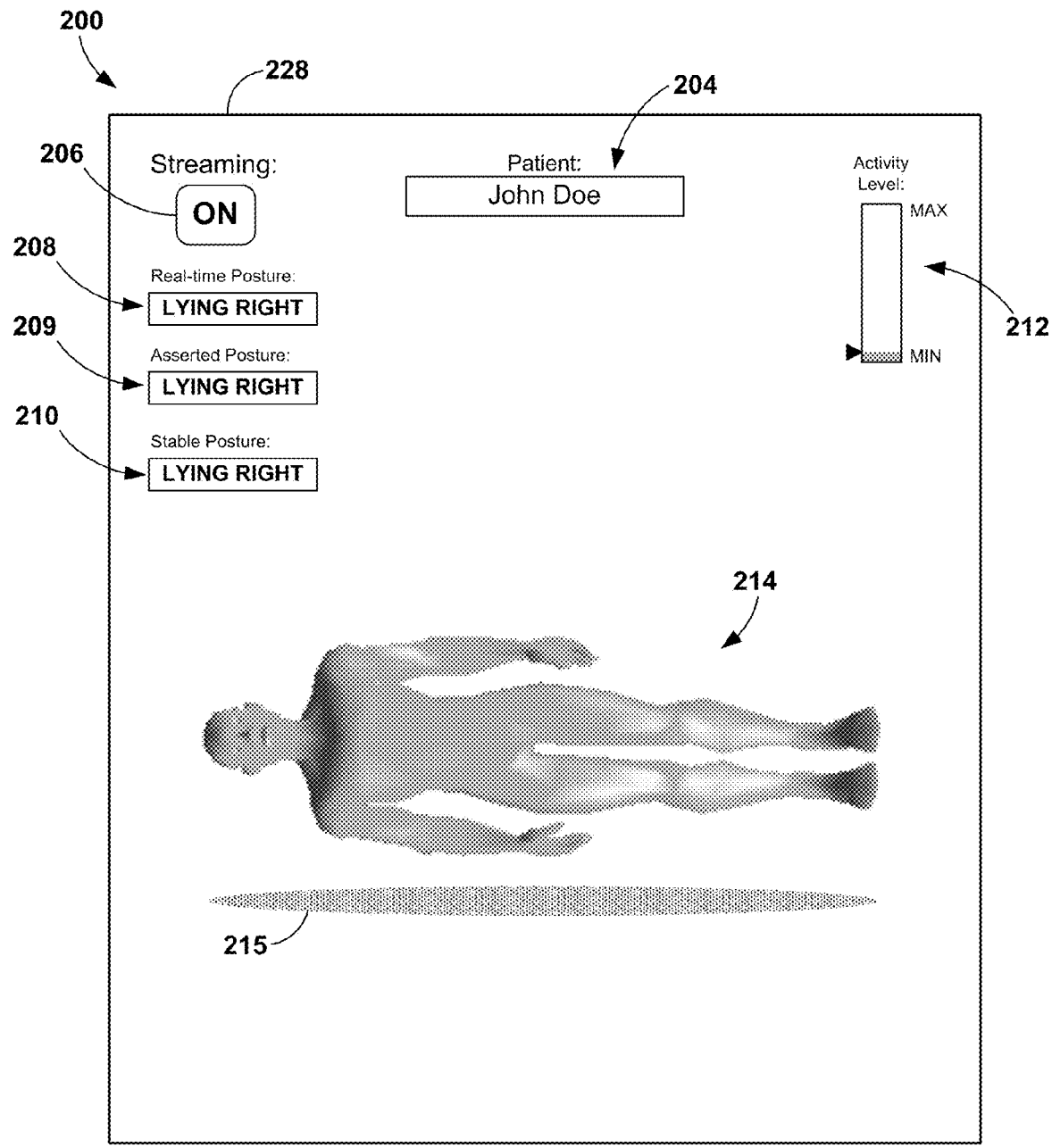

As shown in FIG. 13, screen 228 of user interface 200 indicates that the posture state data streamed (or otherwise transmitted) from IMD 14 has caused user interface 200 to generate and present avatar 214 in a lying right anatomical configuration to represent a current "lying right" posture state of patient 12 for each of the real-time, asserted and stable posture states. The lying right avatar 214 in FIG. 13 is also supplemented by real-time posture text 208, asserted posture state text 209 and stable posture state text 210 each indicating that patient 12 is currently engaged in the "lying right" posture state. Avatar 214 may also be able to be shown in a lying left and lying front, lying front or other postures state configuration detectable by programmer 20 and/or posture state module 86 if the posture state of patient 12 is so detected.

Figure 14:
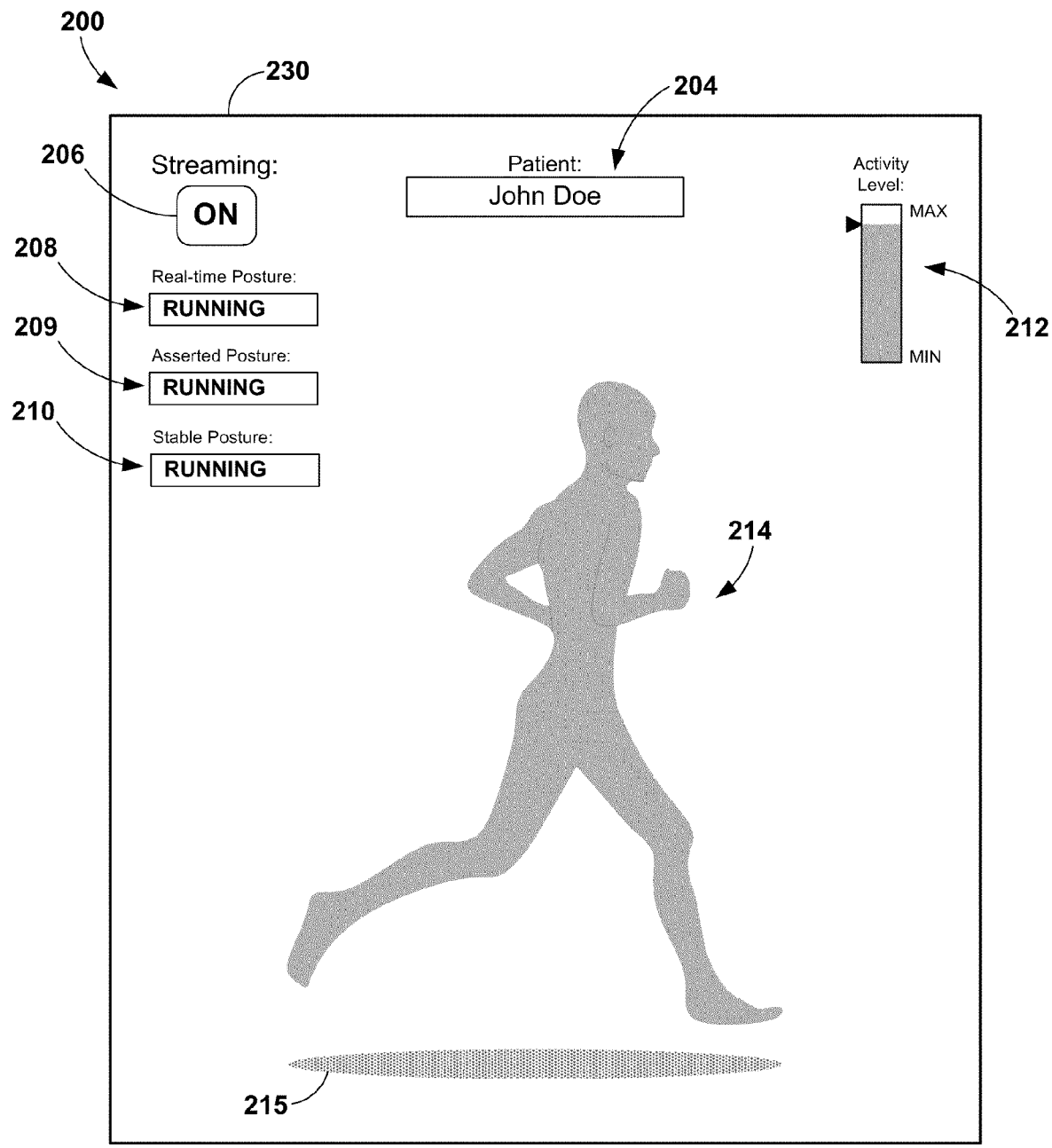

As shown in FIG. 14, screen 230 of user interface 200 presents avatar 214 in a running configuration. The posture state data streamed (or otherwise transmitted) from IMD 14 to programmer 20 indicates that not only is patient 12 in an upright posture, but the detected activity count has increased from that of FIGS. 10-13. Activity level 212 represents this increase in activity count with a bar near the maximum of activity level 212 to reflect a relatively high activity level. In return, user interface 200 has generated and presented avatar 214 in the running configuration to represent a current "running" posture state of patient 12. The running avatar 214 is also supplemented by real-time posture text 208, asserted posture state text 209, and stable posture text 210 each indicating that patient 12 is currently engaged in the "running" posture state.

Other activities may be similarly identified with avatar 214. For example, avatar 214 or other posture state indicators may be shown to reflect a biking or a walking posture state based upon the activity level and orientation of patient 12. In such examples, the configuration of avatar 214 may represent the real-time posture state stable posture state, or asserted posture state of patient 12.

Figure 15:
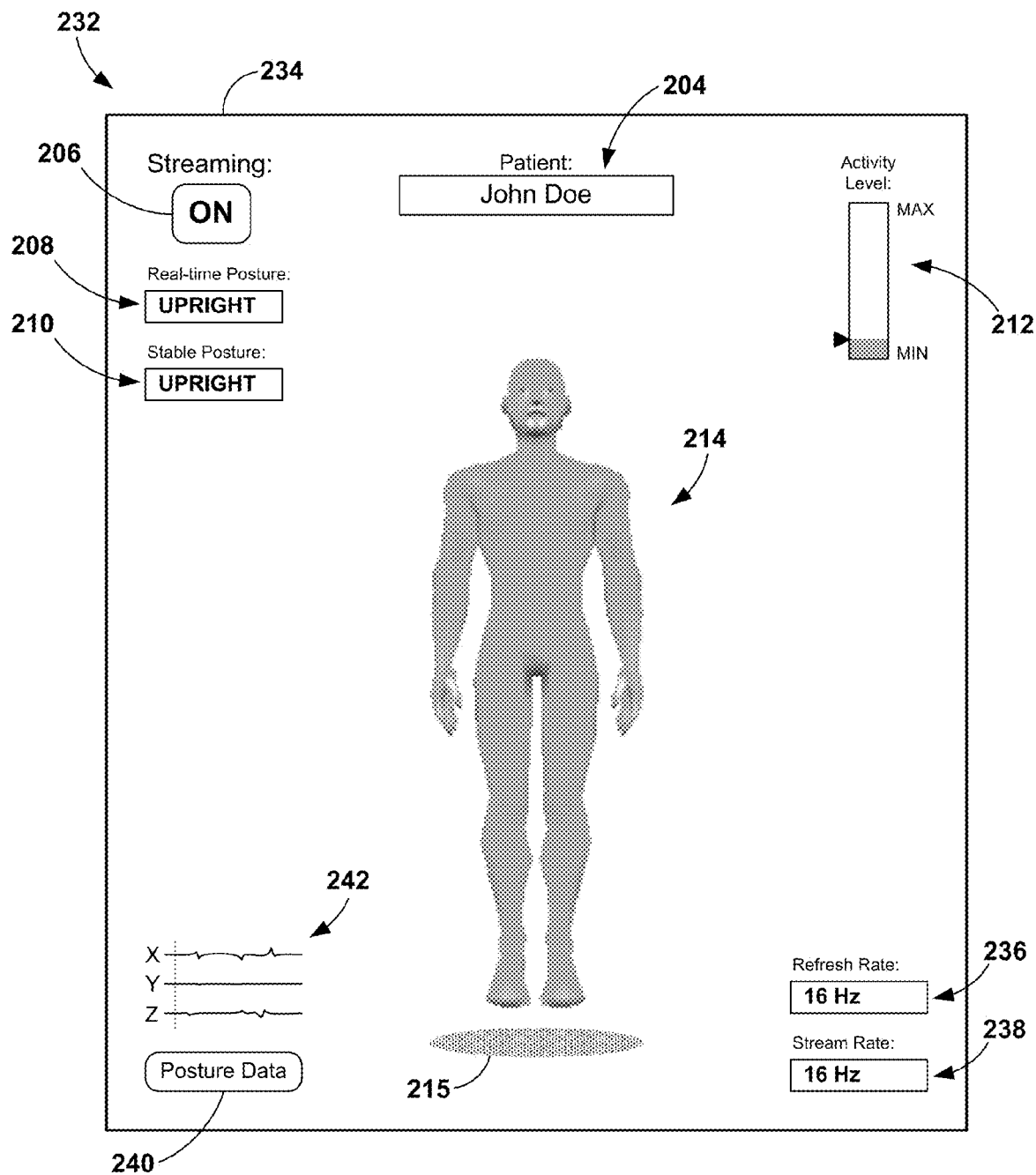
FIG. 15 is a conceptual diagram illustrating an example user interface for displaying an example posture state indicator for a patient based on posture state data.

FIG. 15 is a conceptual diagram illustrating example user interface 232 for displaying avatar 214 and streamed (or otherwise transmitted) posture state data in or near real-time. User interface 232 is substantially similar to user interface 200. However, user interface 232 provides additional information including the raw posture state sensor data in real-time and information detailing the real-time streaming of data. As shown in FIG. 15, screen 234 presents posture data button 240, raw sensor data graph 242, refresh rate indicator 236, and stream rate indicator 238.

If the user desires to monitor the actual raw sensor data for each axis of posture state module 86, the user can select posture data button 240 to display this information. Screen 234 is presenting the raw posture state sensor data in raw data graph 242 as the parameter values for each x, y, and z axis in real-time. Raw sensor data graph 242 is a scrolling graph, but any other types of graphs may be used. In other examples, raw sensor data graph 242 may additionally or alternatively present numerical values for each axis. The user may monitor this raw sensor data to further review and adjust detection algorithm(s) used to generate the real-time posture state, asserted posture state, and/or stable posture state indicated by avatar 214 as well as text indicators 208, 209, and 210.

Screen 234 also presents information about the processing and streaming of posture state data. Refresh rate indicator 236 indicates the current rate at which the posture state of patient 12 is being determined and updated on screen 234. In the example of FIG. 15, the refresh rate is 16 Hz. The stream rate indicator 238 indicates the rate at which posture state data is streamed from IMD 14 to programmer 20. Here, the stream rate is 16 Hz, which is substantially the same as the refresh rate. However, the stream rate and refresh rate may be different. In some examples, the streamed posture state data may be a rolling average or weighted average of detected posture state parameter values, such as, e.g., sampled sensor values. Alternatively, the real-time streamed posture state data may merely be the latest, or most recent, of the sampled data.

Figure 16A:
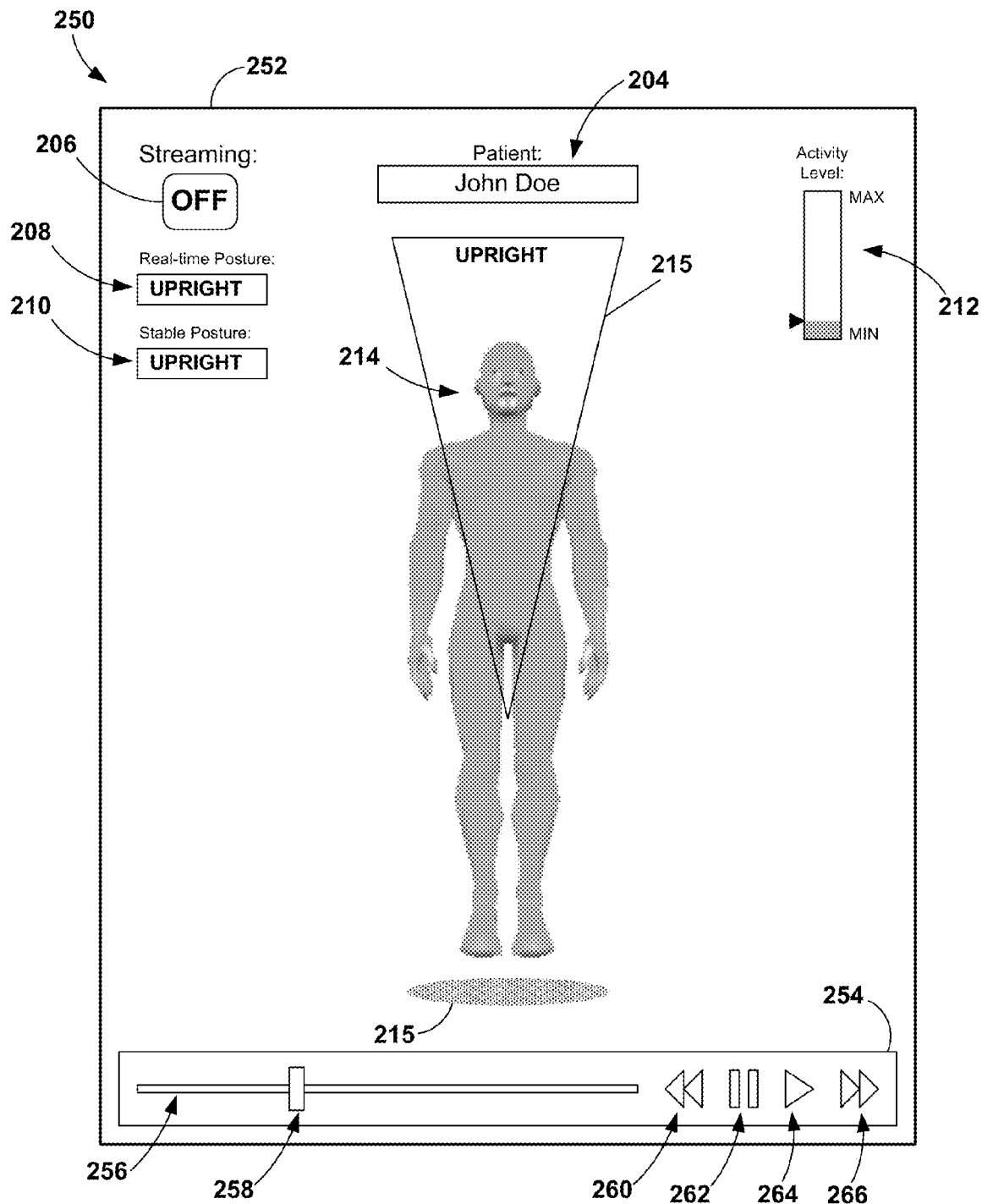
FIGS. 16A and 16B are conceptual diagrams illustrating an example user interface with a playback field that enables a user to review prior posture state data.
Figure 16B:
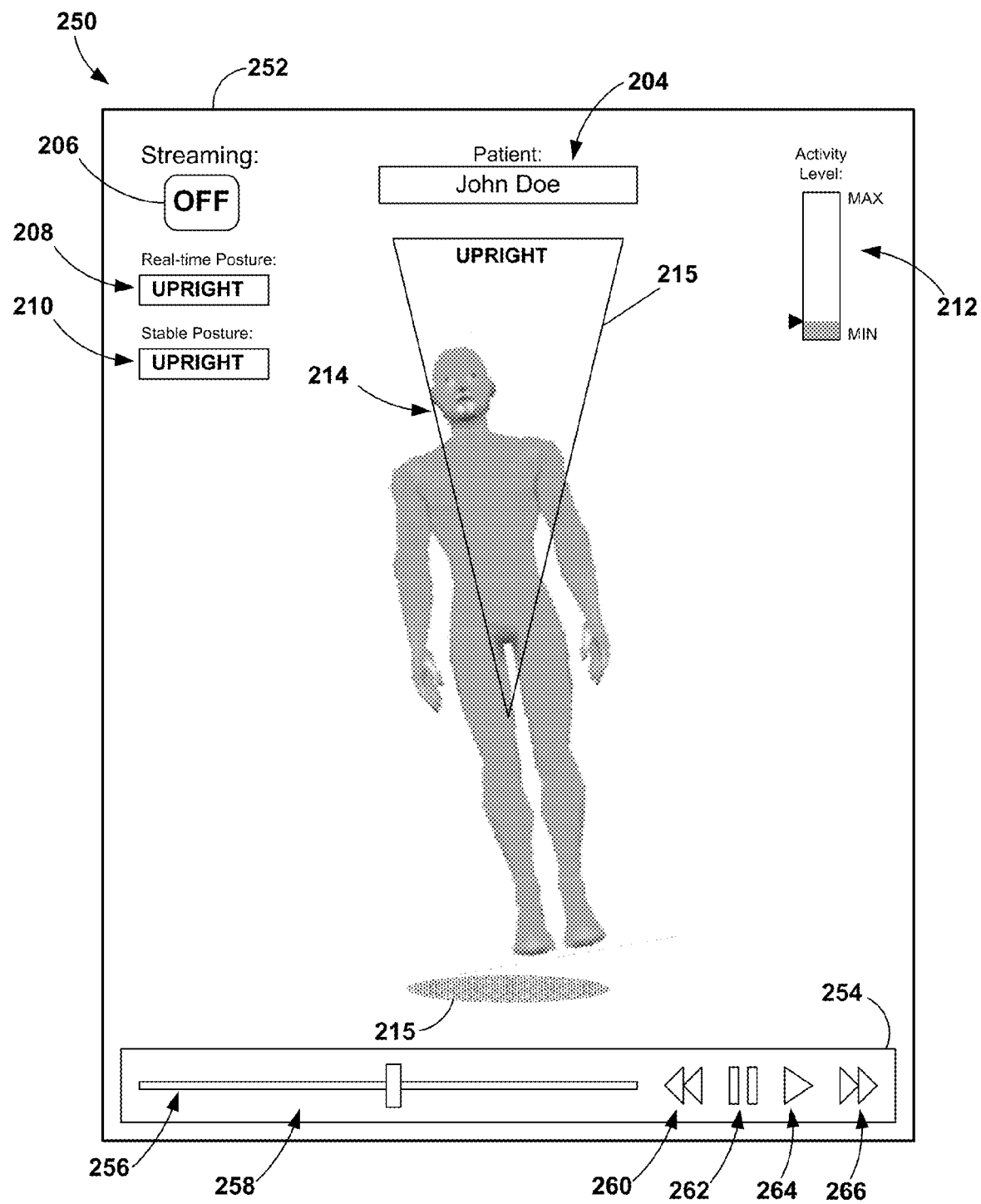

FIGS. 16A and 16B are conceptual diagrams illustrating example user interface 250 with playback field 254 that enables a user to review prior posture state data. User interface 250 is substantially similar to user interface 200 of FIGS. 9-14. However, user interface 250 also includes playback field 254 to facilitate the review of prior posture state data. In some examples, the previously stored posture state data may correspond to a previous session in which programmer 20 presented postures state data in or near real-time to a user. Alternatively, the previously stored data may not have been used to generate posture state indicators for presentation to a user in real-time but instead may have been stored (e.g., in memory 82 of IMD 14 or memory 108 of programmer 20) for later review by a user in a similar fashion. When in playback mode, streaming indicator 206 indicates that streaming is "OFF" because this is a playback mode.

As shown in FIGS. 16A and 16B, screen 252 of user interface 250 includes playback field 254. Playback field 254 allows the user to interact with any of time bar 256, time position 258, reverse button 260, pause button 262, play button 264, or forward button 266 to select a portion of the real-time session to review. The user can select any point on time bar 256 to force time position 258 to jump to that specific time. The user can also select time position 258 and drag the time position to any desired point along time bar 256. Alternatively, the user can select reverse button 260 to move backward in time or forward button 266 to more forward in time. Each selection of either reverse button 260 or forward button 266 may jump time position 258 a certain amount of time. The jump may be a predetermined amount of time or a percentage of the total time represented by time bar 256.

The user may also select play button 264 to progress sequentially through the posture state information as experienced by patient 12. Although the play mode may move in the real-time of prior events, this play may be too slow for effective review. Therefore, the play move may be an accelerated movement through time, either as a present pace or according to the total period of the previous real-time session. If the user wants to pause or stop at a certain time point, the user can select pause button 262.

As time position 258 moves through the time represented by time bar 256, the information displayed by any of avatar 214, real-time posture indicator 208, stable posture indicator 210, and activity level 212 changes according to those values of the specific time. Although avatar 214, real-time posture indicator 208, stable posture indicator 210, and activity level 212 represent posture state data from a previous time, the indicated information concurrently presented on screen 250 is presented on the same temporal basis with one another. In this manner, as user may be able to evaluate temporal relationships between different types of detected posture states (e.g., real-time posture state, asserted posture state, and/or stable posture state) even though the screen is presenting historical posture state data. In the example of FIG. 16, avatar 214 was in the upright posture state at the indicated time along time bar 256. The user may view the exact time, the raw posture state data of that time, or any other details by selecting or hovering over certain spots within screen 252.

FIGS. 16A and 16B illustrate an example in which avatar 214 is configured to conceptually represent the position of a sensed posture state vector within "upright" posture state cone 215. A sensed vector may be calculated using sampled sensor values for x, y, and z axis signals generated, for example, by a three-axis accelerometer. Programmer 20 may orient the position of avatar 204 on screen 250. As shown in FIG. 16A, at the time indicated on playback field 254, the sensed coordinate vector for patient 12 corresponded to an orientation within "upright" posture state cone 215 that is in substantially the center of cone 215. Conversely, as shown in FIG. 16B, at the time indicated on playback field 254, the sensed coordinate vector for patient 12 corresponds to an orientation within "upright" posture state cone 215 that is slightly tilted to an edge of cone 215. Posture cone 215 and/or other defined posture cones may or may not be shown in conjunction with avatar 204 or other graphical indicator of a sensed coordinate vector on screen 250.

The movement of avatar 214 or other visual representation to represent the sensed posture state coordinates may allow a user to evaluate the position of a patient within a posture state rather than presenting all positions for a posture state using an avatar or other visual representation in substantially the same configuration on screen 250. In some examples, such a technique may be used to more precisely portray the position of patient within a more broadly defined posture space. Furthermore, such precision may provide for the movement of avatar or other representation to move fluidly when updated in a continuous manner on screen 250, e.g., compared to that of an avatar that periodically "jumps" between various patient posture states positions based on received posture state data.

Posture state cone 215 displayed on screen 250 provides a reference for position of a patient within the posture space generally and also within "upright" posture cone. In some examples, multiple posture state cones may be overlaid on avatar 214 or avatar may be presented without a graphical representation of one or more posture cones. In some examples, the representation of avatar 214 or other graphical indicator may be presented based on a sensed vector computed, for example, from sampled x, y, and z axis signals to assist a user in defining and/or adjusting posture cones or other regions for posture state detection. One or more examples of graphically manipulating posture zones/cones and parameters (e.g., posture transition times) using an external device may be described in co-pending U.S. Provisional Patent Application 61/293,555, to Davis, et al., filed Jan. 8, 2010, titled "GRAPHICAL MANIPULATION OF POSTURE ZONES FOR POSTURE-RESPONSIVE THERAPY".

Figure 17:
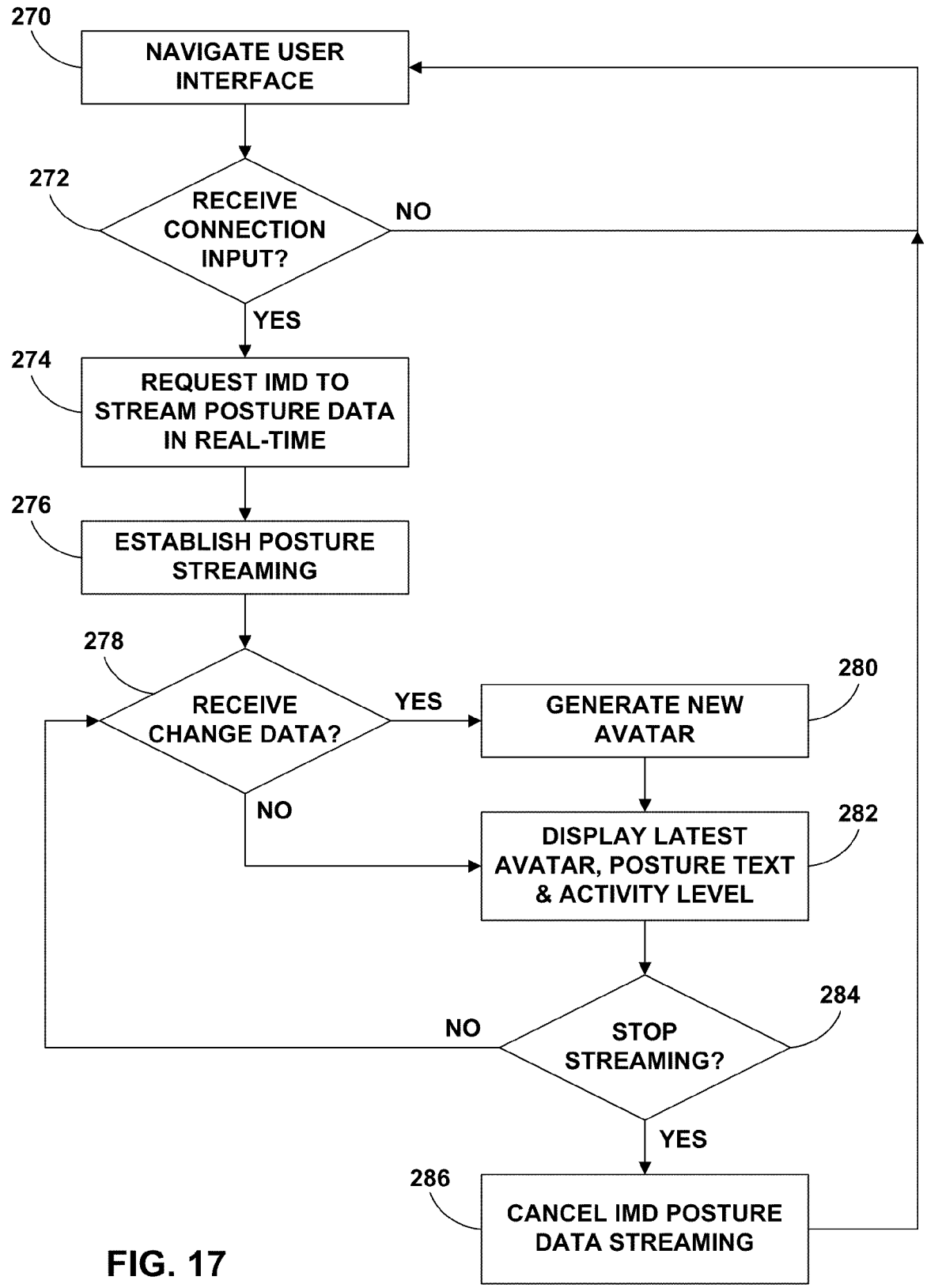
FIG. 17 is a flow chart illustrating an example technique for presenting an example posture state indicator of a patient in or near real-time.

FIG. 17 is a flow chart illustrating an example technique for presenting avatar 214 for patient 12 based upon real-time streamed posture state data. For purposes of illustration, user interface 200 of external programmer 20 and IMD 14 will be described. However, any combination of programmers 20, 30 and 60 could be used with IMD 14 or 26. Also, user interface 232 may alternatively be used. Moreover, while the example technique of FIG. 17 is described with regard to avatar 214, such an example may be used in conjunction with any posture state indicator.

As shown in FIG. 17, the process begins with the user navigating user interface 200 of programmer 20, i.e., the display device (270). If no input to connect with IMD 14 has been received (272), programmer 20 continues to present user interface 200 for navigation (270). Once user interface 200 receives a connection input from the user to initiate real-time streaming from IMD 14 (272), processor 104 transmits a request to IMD 14 to being streaming posture state data in real-time (274). IMD 14 and programmer 20 then establish posture state data streaming in or near real-time through a wireless or wired connection (276).

If programmer 20 receives posture state data from IMD 14 that indicates patient 12 has changed to a different posture state (278), processor 104 generates a new avatar in the appropriate anatomical configuration based upon the streamed posture state data (280). User interface 200 then displays the latest avatar configuration, posture text, and activity levels in real-time as indicated by the posture state data (282). If there is no change to the posture state data (278), user interface 200 continues to present the latest avatar (or other graphical indicator) and posture information to the user (282).

If there is no request by the user to stop streaming (284), programmer 20 continues to check for changes in patient posture state based on the received posture state data (278) and presents the latest appropriate avatar and other posture information (282). If user interface 200 receives an input to stop streaming posture state data and presenting the avatar in real-time (284), then programmer 20 stops updating the avatar and requests that IMD 14 cancels posture state streaming (286). Programmer 20 continues to allow the user to navigate user interface 200 (270).

In addition to this technique for presenting an avatar in real-time according to real-time streamed posture state data, the technique may include any other concepts described herein. For example, user interface 232 may similarly update raw data graph 242 as new posture state data is received from IMD 14 in real-time. Further, the technique may support real-time changes to detection algorithms, re-calibration of posture state module 86, or any other programming functions associated with therapy to patient 12.

Figure 18:
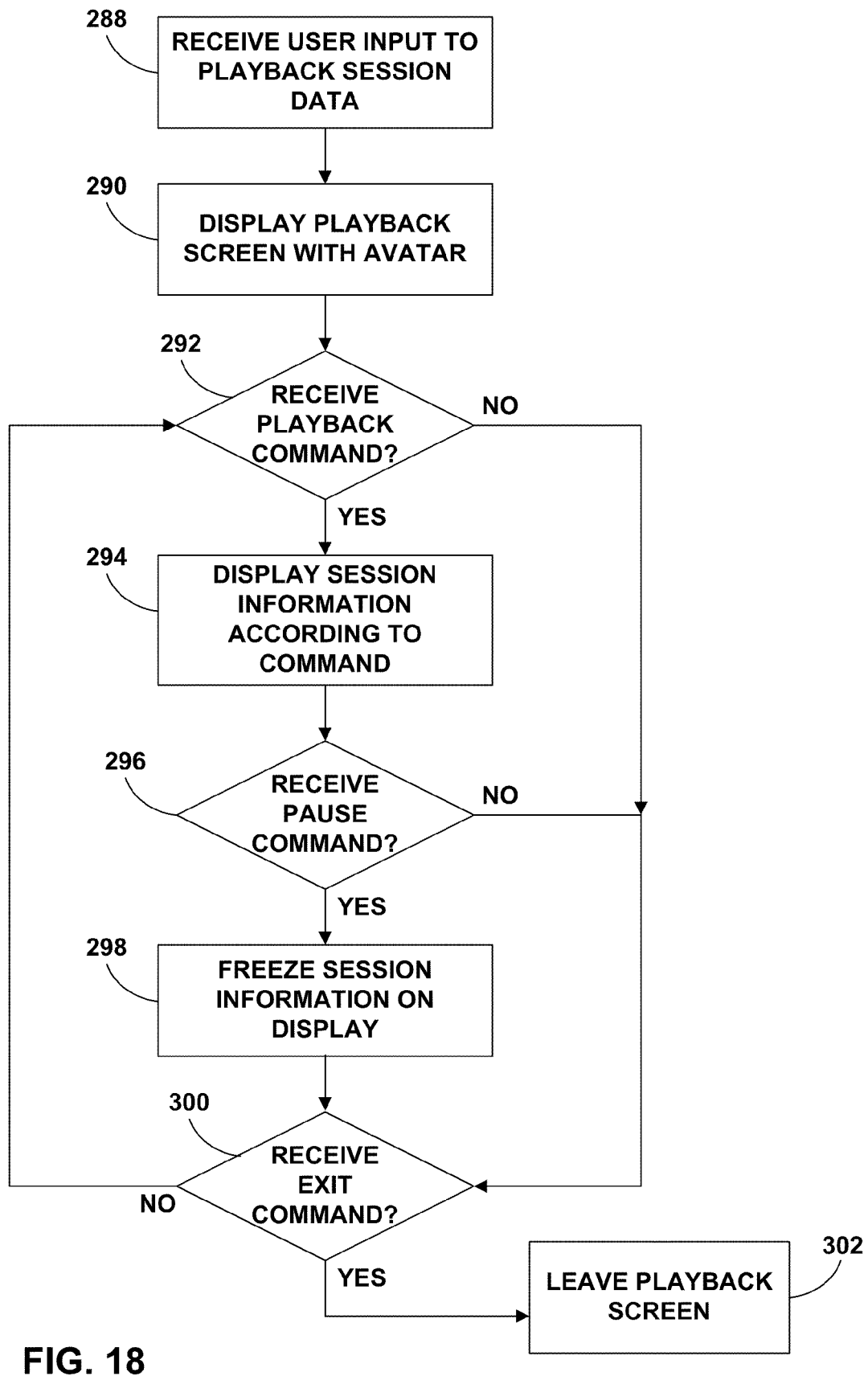
FIG. 18 is a flow chart illustrating an example technique for reviewing a historical posture state data.

FIG. 18 is a flow chart illustrating an example method for reviewing prior posture state data for patient 12. As describe above, the prior posture state data may be from a previous real-time avatar session. For purposes of illustration, user interface 250 of programmer 20 and IMD 14 will be described. However, any combination of programmers 20, 30 and 60 could be used with IMD 14 or 26. Moreover, while the example technique of FIG. 18 is described with regard to avatar 214, such an example may be used in conjunction with any posture state indicator.

As shown in FIG. 18, processor 104 of external programmer 20 retrieves a previous real-time session in which a real-time avatar was presented on programmer 20. This retrieval is done after programmer 20 receives user input to play back previous real-time session data (288). User interface 250 then displays avatar 214 and posture information according to the specified time (290).

If user interface 250 receives a playback command (292), user interface 250 displays the new avatar and other posture information of the new specified time according to the playback command (294). If the playback command was to present a sequence or continual change, user interface 250 continues to change the avatar and posture information presented according to the new specified time. If user interface 250 receives a selection of pause button 262 (296), then user interface 250 freezes the currently displayed avatar and posture information on the display (298). If there is no command received to exit the screen of user interface 250 (300), user interface 250 does not change the displayed avatar and posture information until another playback command is received (292). If user interface 250 receives an exit command from the user (300), user interface 250 exits the screen of user interface 250 and external programmer 20 leaves the playback screen for a different menu (302).

The disclosure describes a system that may be capable of providing many features to a user. For example, presenting a real-time avatar or other posture state indicator may allow a clinician to quickly identify how the medical device is detecting one or more posture states of a patient. If the detected posture state is not accurate, the clinician may re-calibrate or adjust the posture detection algorithm. Further, the real-time avatar or other posture state indicator may aid the clinician in programming therapy that is responsive to various posture states of the patient. The clinician may also be able to review a previous real-time session to determine any problems with therapy after the patient has left the clinic.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a computer-readable medium. Computer-readable media may include non-transitory computer storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that may benefit from the subject matter of this disclosure.

Many embodiments of the disclosure have been described. Various modifications may be made without departing from the scope of the claims. These and other embodiments are within the scope of the following claims.

The invention claimed is:

1. A method comprising:
receiving posture state data for a patient from a medical device;
determining a first posture state of the patient at a time based on the posture state data using a first detection criteria;
determining a second posture state of the patient at the time based on the posture state data using a second detection criteria different from the first detection criteria; and
presenting an indicator indicative of the determined first posture state and second posture state,
wherein at least one of the receiving, determining the first posture state, determining the second posture state, and presenting is performed by at least one processor.

2. The method of claim 1, wherein the first posture state and second posture state include at least one of real-time patient posture state, asserted patient posture state, and stable patient posture state.

3. The method of claim 1, wherein the medical device is configured to deliver therapy to the patient.

4. The method of claim 1, wherein presenting the indicator comprises presenting one or more graphical representations representative of the first posture state and the second posture state.

5. The method of claim 1, wherein the received posture state data is transmitted from the medical device in real-time or near real-time with generation of the posture state data.

6. The method of claim 1, further comprising presenting at least one of a posture state text, an activity level, and a raw signal data graph based upon the posture state data.

7. The method of claim 1, wherein presenting an indicator indicative of the determined first posture state and second posture state comprises presenting a stable posture state indication indicative of a stable posture state used by the medical device to deliver therapy and presenting an unstable posture state indication indicative of an unstable posture state not used by the medical device to delivery therapy.

8. The method of claim 7, wherein the unstable posture state comprises at least one of a real-time posture state or asserted posture state.

9. The method of claim 1, wherein receiving posture state data for the patient from the medical device comprises receiving posture state data for the patient from the medical device at a stream rate between about 1 Hz and about 3 Hz.

10. The method of claim 1, wherein the indicator indicative of the determined first posture state and second posture state is at least one of an upright posture state indicator, a reclining posture state indicator, a lying back posture state indicator, a lying front posture state indicator, a lying left posture state indicator, a lying right posture state indicator, a running posture state indicator, and a biking posture state indicator.

11. The method of claim 1, further comprising displaying a playback field configured to allow a user to review historical posture state data on a temporal basis.

12. The method of claim 1, further comprising delivering electrical stimulation therapy to the patient according to the posture state data.

13. A system comprising:
a user interface; and
at least one processor configured to receive posture state data from a medical device, determine a first posture state of the patient at a time based on the posture state data using a first detection criteria; determine a second posture state of the patient at the time based on the posture state data using a second detection criteria different from the first detection criteria,
control the user interface to present an indicator indicative of the determined first posture state and second posture state.

14. The method of claim 1, wherein the first posture state is different from the second posture state.

15. The method of claim 1, wherein presenting an indicator indicative of the determined first posture state and second posture state comprising presenting a first indicator indicative of the first posture state at substantially a same time as presenting a second indicator of the second posture state.

16. The system of claim 1, wherein the user interface presents a first indicator indicative of the first posture state at substantially a same time as presenting a second indicator of the second posture state.

17. The system of claim 13, wherein the first posture state and second posture state include at least one of real-time patient posture state, asserted patient posture state, and stable patient posture state.

18. The system of claim 13, wherein the medical device is configured to deliver therapy to the patient.

19. The system of claim 13, wherein the user interface presents the indicator by at least presenting one or more graphical representations representative of the first posture state and the second posture state.

20. The system of claim 13, wherein the processor receives the posture state data from the medical device in real-time or near real-time with generation of the posture state data.

21. The system of claim 13, wherein the user interface is configured to present at least one of a posture state text, an activity level, and a raw signal data graph based upon the posture state data.

22. The system of claim 13, wherein the user interface presents a stable posture state indication indicative of a stable posture state used by the medical device to deliver therapy and presents an unstable posture state indication indicative of an unstable posture state not used by the medical device to delivery therapy.

23. The system of claim 22, wherein the unstable posture state presented by the user interface comprises at least one of a real-time posture state or asserted posture state.

24. The system of claim 13, wherein the processor receives the posture state data from the medical device at a stream rate between about 1 Hz and about 3 Hz.

25. The system of claim 13, wherein the user interface presents at least one of an upright posture state indicator, a reclining posture state indicator, a lying back posture state indicator, a lying front posture state indicator, a lying left posture state indicator, a lying right posture state indicator, a running posture state indicator, and a biking posture state indicator.

26. The system of claim 13, wherein the user interface is configured to display a playback field configured to allow a user to review historical posture state data on a temporal basis.

27. The system of claim 13, wherein the medical device is configured to deliver electrical stimulation therapy to the patient according to the posture state data.

28. The system of claim 13, wherein the first posture state is different from the second posture state.

29. A system comprising:
means for receiving posture state data for a patient from a medical device;
means for determining a first posture state of the patient at a time based on the posture state data using a first detection criteria;
means for determining a second posture state of the patient at the time based on the posture state data using a second detection criteria different from the first detection criteria; and
means for presenting an indicator indicative of the determined first posture state and second posture state.

30. A non-transitory computer-readable storage medium comprising instructions that cause one or more processors to:
receive posture state data for a patient from a medical device; and
determine a first posture state of the patient at a time based on the posture state data using a first detection criteria;
determine a second posture state of the patient at the time based on the posture state data using a second detection criteria different from the first detection criteria;
control a user interface to present an indicator indicative of the determined first posture state and second posture state.

* * * * *

UNITED STATES PATENT AND TRADEMARK OFFICE
CERTIFICATE OF CORRECTION

PATENT NO. : 8,579,834 B2  
APPLICATION NO. : 12/985965  
DATED : November 12, 2013  
INVENTOR(S) : Davis et al.

Page 1 of 1

It is certified that error appears in the above-identified patent and that said Letters Patent is hereby corrected as shown below:

In the Claims

Col. 49, Line 42: "the system of claim 1" should read --the system of claim 13--

Signed and Sealed this
Twenty-ninth Day of September, 2015

Michelle K. Lee
*Director of the United States Patent and Trademark Office*